(12) United States Patent  (10) Patent No.: US 12,042,267 B2
Dykstra  (45) Date of Patent: Jul. 23, 2024

(54) DETERMINING ODORANT DETECTION IN ARTHROPODS

(71) Applicant: Technology SG, L.P., West Conshohocken, PA (US)

(72) Inventor: Thomas M. Dykstra, Gainesville, FL (US)

(73) Assignee: TECHNOLOGY SG, L.P., West Conshohocken, PA (US)

( * ) Notice: Subject to any disclaimer, the term of this patent is extended or adjusted under 35 U.S.C. 154(b) by 719 days.

(21) Appl. No.: 17/274,107

(22) PCT Filed: Sep. 6, 2019

(86) PCT No.: PCT/US2019/049936
§ 371 (c)(1),
(2) Date: Mar. 5, 2021

(87) PCT Pub. No.: WO2020/051441
PCT Pub. Date: Mar. 12, 2020

(65) Prior Publication Data
US 2021/0356390 A1  Nov. 18, 2021

Related U.S. Application Data

(60) Provisional application No. 62/728,488, filed on Sep. 7, 2018.

(51) Int. Cl.
*A61B 5/11* (2006.01)
*A61B 5/00* (2006.01)
(Continued)

(52) U.S. Cl.
CPC .......... *A61B 5/1105* (2013.01); *A61B 5/4011* (2013.01); *G01N 21/251* (2013.01);
(Continued)

(58) Field of Classification Search
CPC .... A64B 5/1105; A64B 5/4011; G01N 21/31; G01N 2021/3129; A01M 1/02; A01M 1/10
See application file for complete search history.

(56) References Cited

U.S. PATENT DOCUMENTS 9,173,388 B2 * 11/2015 Canfield ............... A01M 1/145
2003/0151006 A1 * 8/2003 Dykstra ............... A01M 1/023
250/493.1

(Continued)

FOREIGN PATENT DOCUMENTS

KR  10-2011-0008571 A  1/2011

OTHER PUBLICATIONS

International Search Report and Written Opinion from International Application No. PCT/US2019/049936 dated Dec. 30, 2019, 10 pages.

(Continued)

*Primary Examiner* — Richard G Davis
(74) *Attorney, Agent, or Firm* — Sterne, Kessler, Goldstein & Fox P.L.L.C.

(57) ABSTRACT

According to various embodiments, systems and methods for determining carbon dioxide detection in arthropods. An embodiment may include determining at least one resonant frequency of an arthropod sensory organ and an absorption spectrum of at least one odorant. A frequency filter may be applied to the absorption spectrum to eliminate frequencies below a given intensity value. Of the frequencies remaining from the absorption spectrum, those frequencies corresponding to relative peaks in absorption intensity may be selected. An olfactory chord including a group of the selected frequencies corresponding to the relative peaks in absorption intensity with at least one specific frequency that matches the at least one resonant frequency of the arthropod sensory organ. Additionally, at least one radiation source may be (Continued)

configured to emit electromagnetic radiation corresponding to the olfactory chord.

16 Claims, 13 Drawing Sheets

(51) Int. Cl.
  *G01N 21/25* (2006.01)
  *G01N 21/31* (2006.01)
  *G01N 21/01* (2006.01)

(52) U.S. Cl.
  CPC ........... *G01N 21/255* (2013.01); *G01N 21/31* (2013.01); *G01N 2021/0137* (2013.01); *G01N 2021/3129* (2013.01)

(56) References Cited

U.S. PATENT DOCUMENTS

| | | | |
|---|---|---|---|
| 2003/0165879 A1 | 9/2003 | Woods et al. | |
| 2014/0259858 A1* | 9/2014 | Canfield | A01M 1/04 43/2 |
| 2015/0051882 A1* | 2/2015 | Canfield | G16C 20/50 703/2 |

OTHER PUBLICATIONS

Hansson et al., "Evolution of Insect Olfaction," Neuron 72, Dec. 8, 2011, 14 pages.

\* cited by examiner

**Schematic Diagram for CO₂ Olfactory Chord Emitter to Target Olfactory Receptors of Malaria Mosquito *Anopheles Gambiae***

FIG. 13

DETERMINING ODORANT DETECTION IN ARTHROPODS

BACKGROUND

The science of olfaction has long created confusion for researchers. Many theories have surfaced to explain the sequence of events known as "smell." Of these theories, two have survived the test of time: Shape Theory and Vibrational Theory.

The Shape Theory maintains that an odorant is recognized by a protein receptor due to its shape. In this theory, the odorant fits into a pocket of the receptor thus instigating the receptor to initiate an action potential in a sensory nerve cell. This is an established event in pharmacology and has played a large role in why sensory biologists have assumed that the same process occurs in olfaction.

Vibrational Theory received some support in mammals when electron tunneling was applied to olfaction (Turin, 1996). This theory suggested that the odorant would fit into a pocket of the receptor, but be "read" by its vibrational signature and not simply by virtue of its simply fitting into the receptor's pocket. It differed from the Shape Theory in how the odorant was fundamentally recognized, but it was similar to the Shape Theory in that physical contact between the odorant and the receptor is a necessary prerequisite. Additional evidence was presented by Franco et al. (2011) showing that insects smell electromagnetically (vibrationally). These researchers showed that insects detect smells using an electromagnetic vibrational component, assuming existence of an electron tunneling mechanism.

Arthropods (including insects) smell predominantly using their antennae. The shape theory maintains that odorant molecules make contact with the antenna, impact with sensilla on the antennae, enter these sensilla via sensillar pores, possibly also binding with an Odorant Binding Protein (OBP) and diffusing through the sensillar lymph so as to reach a dendritic membrane in less than one millisecond. It is on the dendritic membrane that these chemosensory receptors may be found. These chemosensory receptors on the dendritic membrane are proteins that may be classified into groups such as Odorant Receptors (ORs), Gustatory Receptors (GRs), Ionotropic Receptors (IRs), Odorant Receptor Co-Receptors (ORCOs), and Sensory Neuron Membrane Proteins (SNMPs), for example.

These chemosensory receptors respond to odorants. However, no evidence has been presented to show that contact is ever made between the activating odorant and the receptor. Following the laws of physics, it is unlikely that any odorant, not even a small molecule such as carbon dioxide, would diffuse through the sensillar pores and then the sensillar lymph to reach the dendritic membrane within one millisecond. Rather, it is more reasonable to assume that no odorant directly contacts the dendritic membrane or its associated membrane proteins.

Despite this likely lack of contact, it is readily observable that the receptors appear to respond to these odorants (activation). Yet, there is no clear evidence that the odorants actually touch the dendritic membrane (contact). If the receptors can be activated by odorants, but no contact is made between the odorant and the receptor, then the receptors are responding to the odorants over some unknown distance. Electromagnetic waves are likely the cause.

Physics shows generally how electromagnetic waves are picked up by radio antennas. Arthropod antennae are in fact dielectric resonator antennas (dielectric antennas); thus, the antenna foundation has already been laid. Providing for an antenna to collect energy is a first step in understanding how arthropods smell, but specifically how the collected energy is processed in the sensilla/antennae has not been directly discussed in the scientific literature.

BRIEF DESCRIPTION OF THE DRAWINGS

The accompanying drawings are incorporated herein and form a part of the specification.

Utilizing cross-spectrum analysis in software that may correlate proteins with absorption spectra, e.g., Resonant Recognition Model (RRM) software, Gustatory Receptor #2 in *Aedes aegypti* is crossed against itself 5×.

FIG. 13 is a schematic diagram of an example emitter 1300, according to some embodiments.

In the drawings, like reference numbers generally indicate identical or similar elements. Additionally, generally, the left-most digit(s) of a reference number identifies the drawing in which the reference number first appears.

DETAILED DESCRIPTION

Provided herein are system, method and/or computer program product embodiments, and/or combinations and sub-combinations thereof, for determining odorant detection in arthropods.

If specific energy is collected by the sensilla/antennae, then it follows that this collected energy should in turn activate the receptors. In order for this mechanism to function properly, the odorant's emission frequencies must match the receptor's absorption frequencies. Hence, one must compare the emission frequencies of odorants with the absorption frequencies of receptors in order to ascertain if they overlap. This is the science of resonance. By demonstrating resonance, a mechanism for a Vibrational Theory can be shown as it relates to arthropods not requiring any physical contact between odorant and receptor.

It is possible to predict absorption frequencies of any protein or nucleic acid. For a protein, one may enter the amino acid sequence of the protein into a program, such as Resonant Recognition Model (RRM) software, for example, or other computational algorithms configured to correlate absorption frequencies with molecules of specific chemical compounds. Absorption frequencies may then be calculated and output. RRM in general measures flow of electrons along protein molecules, similar to conductance of electrons along conductors. Software based on the principles of RRM may automatically predict absorption frequencies of specific chemical compounds based on descriptions of their molecular structures, without requiring direct experimentation with spectral analysis (spectral analysis may also be done instead of or in addition to RRM for objective results and verification). An example RRM software tool useful in embodiments of the present invention is the RRM software tool developed and sold by AMALNA Consulting in Australia. Further explanation of RRM and how molecules may be mathematically correlated with their absorption frequencies is discussed in at least the references cited herein authored by I. Cosic, for example. All references cited herein are incorporated by reference in their entirety.

Sequences of known proteins are available from multiple sources (NCBI, UniProt/Swiss-Prot, VectorBase, etc.). For these proteins, relevant frequencies from the visible (400-700 nm) to the infrared range (up to ~100 μm) absorption spectra may be determined, such as by experimentation, calculation, and/or table lookups. For evaluating olfaction (determining whether a chemical compound is detected by a given arthropod or arthropod species), proteins corresponding to specific dendritic membranes in the given arthropod species are of interest. Since there may be multiple copies of each protein receptor on a given dendritic membrane, the individual spectra may be self-crossed 5×, for example, to simulate the biology more closely. An example of an individual spectrum is presented below in FIG. 1.

FIG. 1 is an individual spectrum. For a given species, there may be a number of different GRs (gustatory receptors). This spectrum represents Gustatory Receptor #2 from the mosquito, *Aedes aegypti*, as an example, and may be self-crossed 5× by utilizing a cross-spectrum analysis, such as provided in a Cross Spectrum feature of RRM software, for example. After calculating these initial spectra, the relative peaks may be automatically calculated and converted to wavelengths (e.g., nm, mm, etc.) or to wavecounts or wavenumbers per unit length (e.g., $mm^{-1}$, $cm^{-1}$, etc.). Each peak amplitude may also be listed in table format.

Arthropod chemoreceptors can be analyzed using RRM software, for example. To analyze the pertinent receptor proteins, one may use the arthropod's sequenced genome (or a portion thereof) followed by at least one translation or annotation of proteins corresponding to relevant cells, parts, and/or sensory organs of the given arthropod (transcriptome analysis). Over 320 insect genomes have been determined thus far, but not all of them have their chemoreceptors annotated, such as via transcriptome analysis. Still, there are some types of chemoreceptor analyses that can be completed based on incomplete sets of information.

Carbon Dioxide Detection in Arthropods

Carbon dioxide ($CO_2$) is one test example of a molecule to begin an analysis of how arthropod species detect odorants. Carbon dioxide is a small molecule with only three atoms. The $CO_2$ molecular structure has a linear shape, thus reducing the resulting vibrational frequencies. There are 22 frequencies associated with carbon dioxide (which may be collected from multiple sources ranging from $CO_2$ lasers to satellite technology measuring $CO_2$ on planetary moons, for example). Additionally, the way carbon dioxide detection works may be at least partly understood, at least in insects and other arthropods, along with which receptors are associated with $CO_2$ detection.

As previously discussed, the absorption frequencies can be determined from the amino acid sequence using specially programmed mathematical software packages, e.g., custom scripts or programs to perform transformations or combinations of calculations, or by configurations of commonly available software, e.g., Octave, MATLAB, R, RRM software, to name a few non-limiting examples. These frequencies can be analyzed both individually (FIG. 1) and in concert with one another (FIG. 2). After obtaining the individual spectra, the individual spectra of the relevant receptors, such as the three GRs shown in the example of FIG. 2, can be run against one another by crossing them. The new spectrum emphasizes common peaks and reduces non-related peaks. This analysis can be undertaken because all three GRs are on the same dendritic membrane in a particular sensillum and are capable of influencing or augmenting one another as a result of their proximity.

FIG. 2 is a composite spectrum featuring the multiplication of GR1, GR2, and GR3 for the mosquito species *Aedes aegypti*. The receptors act both as individual units (absorbing energies as their structures permit), and they can also work together owing to their presence in a common membrane (where common absorbencies can be amplified). This arrangement is akin to a single cantor at a performance versus an entire choir. Each cantor in a choir makes an individual contribution that cannot be ignored (tenor, soprano, etc.), but the choir combines to make an apparent new sound, a chorus, which can be readily differentiated from the individual cantors.

Thus, in some embodiments, analysis may focus not only on each frequency absorbed by each GR, but also on any interactions, such as the amplification of common peaks. Therefore, the three individual GR graphs (similar to FIG. 1) may be added to the composite graph (as represented in FIG. 2), which is finally depicted as a bar graph in FIGS. 3-5. The bar graphs in these figures can represent a type of "olfactory chord" (defined here as a combination of frequencies used by a receptor to detect a chemical compound) for three mosquito species in relation to carbon dioxide. In further embodiments, such spectra may be analyzed for receptors of any arthropod species in relation to any other molecule, for example, to water, pheromones, plant odorants, and so on. To aid analysis with respect to another molecule or molecules, one may obtain relevant absorption frequencies for the given molecule(s). These absorption frequencies may be available via public resources (e.g., libraries, journals, online databases such as via the Internet, etc.), private resources (e.g., internal knowledge bases, research repositories, etc.). Alternatively, or where these frequencies are yet unknown, the absorption frequencies may be determined via laboratory experiments utilizing various spectrometers (e.g., UV-Vis, FT-IR, Raman, etc.).

Figure 3:
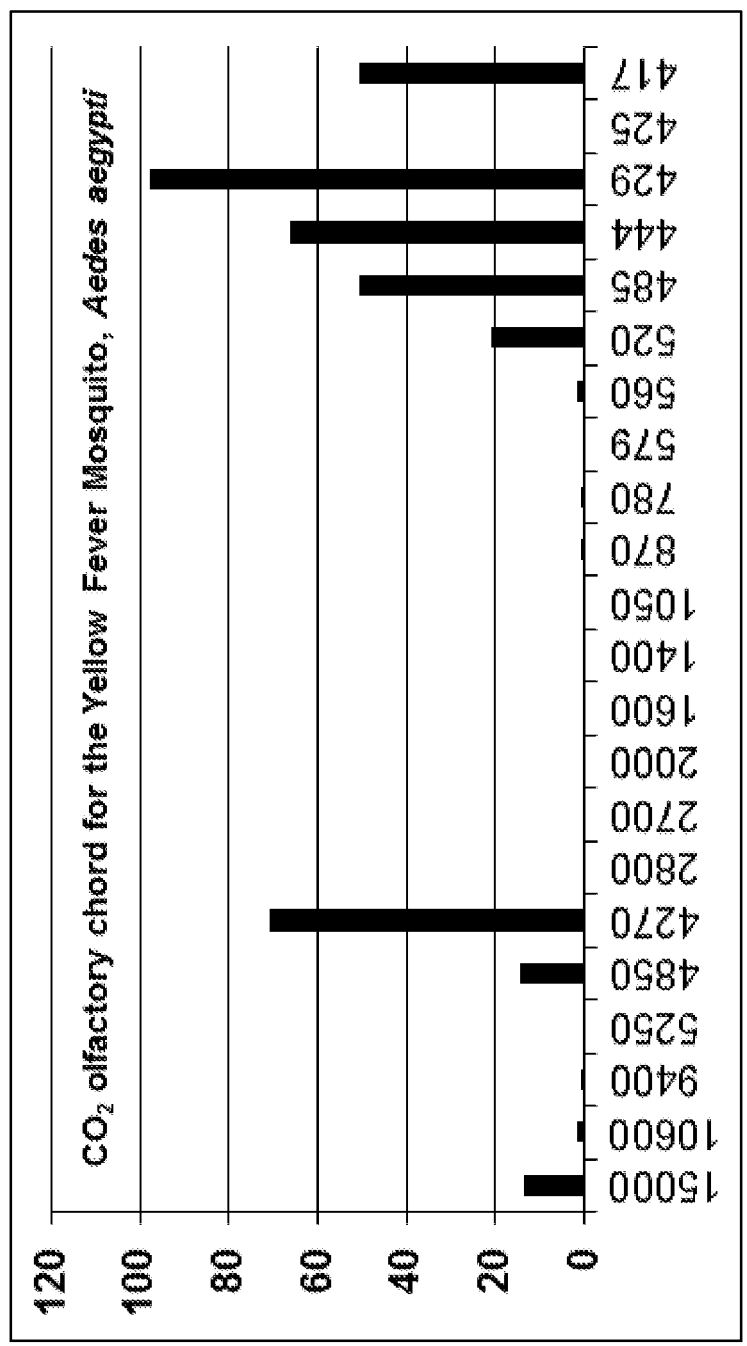
FIG. 3 is a carbon dioxide olfactory chord for *Aedes aegypti*. Thirteen peaks are displayed with their relative intensities. Here, the weighted sum of the intensities is 389.7.
Figure 4:
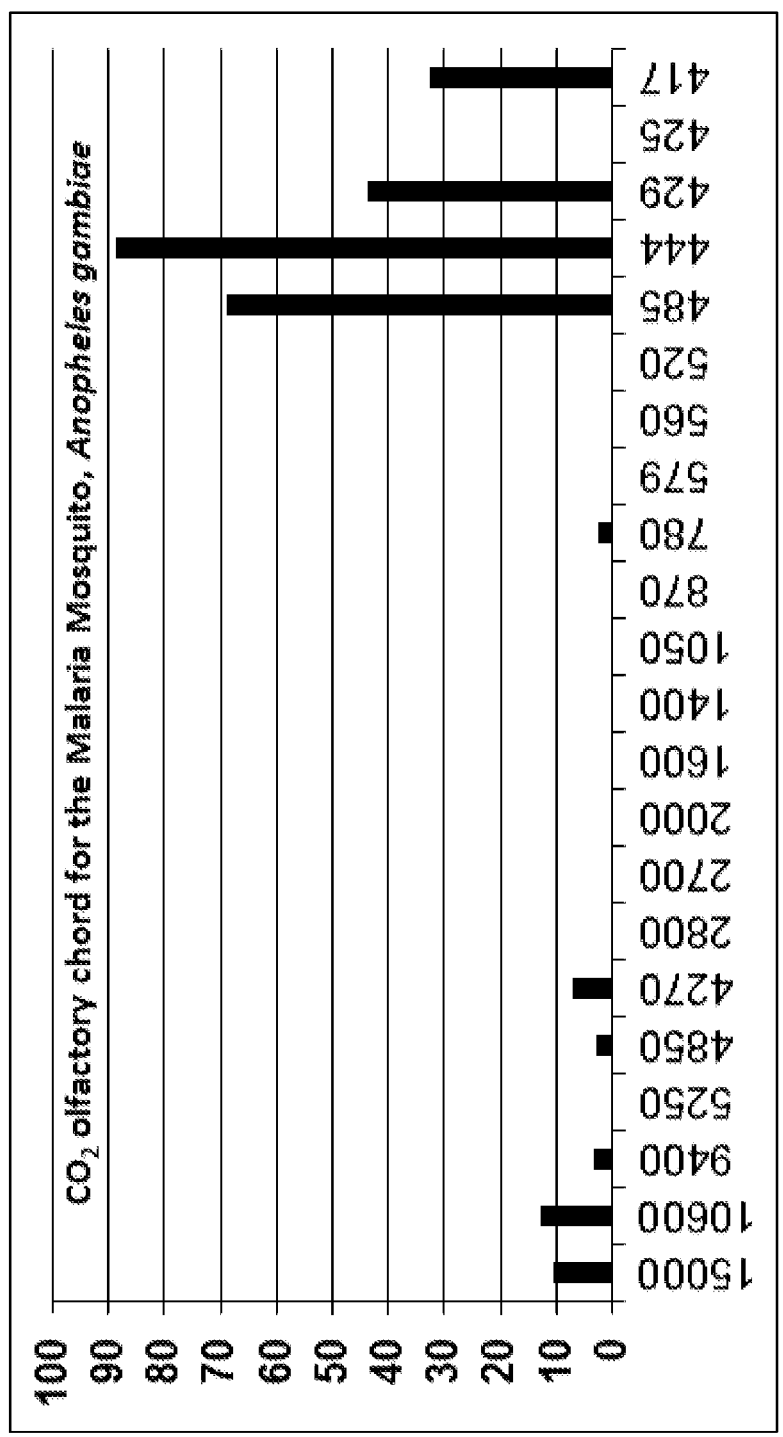
FIG. 4 is a carbon dioxide olfactory chord for *Anopheles gambiae*. Ten peaks are displayed with their relative intensities. Here, the weighted sum of the intensities is 273.2.
Figure 5:
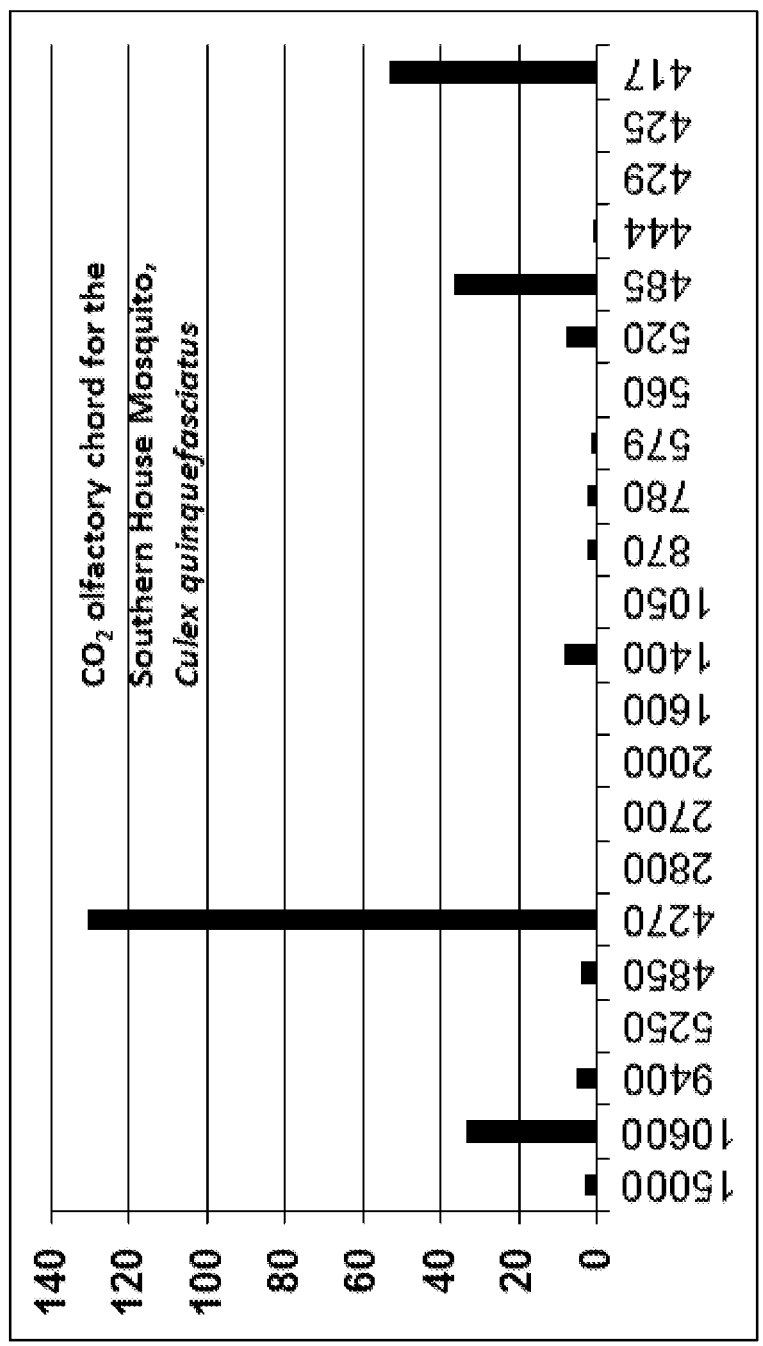
FIG. 5 is a carbon dioxide olfactory chord for *Culex quinquefasciatus*. Thirteen peaks are displayed with their relative intensities. Here, the weighted sum of the intensities is 289.0.

By way of protein listings corresponding to olfaction receptors in arthropods, it is now possible to link species with corresponding frequencies of electromagnetic radiation from emission spectra or absorption spectra of these olfactory receptor proteins. Such mappings of frequencies or wavelengths may be calculated and efficiently reduced to smaller sets of frequencies, according to enhanced techniques and embodiments described herein. FIGS. 3-5 show some of these mappings with respect to three mosquito species, for example.

FIG. 3 is a carbon dioxide olfactory chord for *Aedes aegypti*. Thirteen peaks are displayed with their relative intensities. Here, the sum of the intensities is 389.7.

FIG. 4 is a carbon dioxide olfactory chord for *Anopheles gambiae*. Ten peaks are displayed with their relative intensities. Here, the sum of the intensities is 273.2.

FIG. 5 is a carbon dioxide olfactory chord for *Culex quinquefasciatus*. Thirteen peaks are displayed with their relative intensities. Here, the sum of the intensities is 289.0.

The bar graphs shown in FIGS. 3-5 bear a passing resemblance to a musical chord, i.e., a group of (often three or more) notes sounded together, such as one would find on a musical instrument where multiple notes may be combined to contribute to a particular sound or harmonic effect. Thus, these bar graphs of FIGS. 3-5 may be referred to as representing "olfactory chords" in terms of groupings of electromagnetic absorption frequencies.

In a musical chord, each of the individual sounds contributes to a musical chord, just as each frequency peak contributes to the olfactory chord. Also, each note in a musical chord can differ in intensity, such as hitting some piano keys harder or softer than others in a piano chord. Similarly, the individual peaks of an olfactory chord differ in amplitude (intensity). It is the striking or not striking of certain piano keys that contributes to the playing of specific music, just as certain frequencies contribute to an olfactory chord due to the presence or absence of these olfactory components. Thus, for purposes of analogy, the varied amplitudes of the individual peaks displayed in the various olfactory chords (FIGS. 3-5) may be thought of as a musical chord with some notes being louder or softer than others.

The olfactory chord may be considered to be both a digital code and an analog code. The "on-off" nature of the various peaks (at specific frequencies) resembles the digital code, while the intensity of the peaks resembles an analog code. There is unprecedented precision by combining both digital and analog components in this way. By convention, no two musical chords need be the same, just as near-infinite combinations of notes and chords can be played on a piano. Likewise, there may be a near-infinite number of ways to detect a given odorant. Also, different species may detect carbon dioxide in different ways, even in the same family or genus, as is evident from the bar graphs of "olfactory chords" shown in the drawings presented herewith.

FIGS. 3-5 feature 22 known carbon dioxide frequencies as a function of their peak amplitudes. Not all of these 22 peaks are detected by the 2 or 3 carbon dioxide receptors in a given species. But the presence or absence (digital code) of each of the 22 peaks can be observed as it relates to a particular insect species. Each of FIGS. 3-5 can help visualize the olfactory chords for each of the three most studied mosquitoes in the world, *Aedes aegypti* (the Yellow Fever Mosquito), *Anopheles gambiae* (the Malaria Mosquito), and *Culex quinquefasciatus* (the Southern House Mosquito).

Thus far, over 200 spectra have been analyzed for investigating known carbon dioxide receptors in mosquitoes and other arthropods, and the same carbon dioxide peaks may appear repeatedly. Not all of the peaks are of the same intensity from one species to the next, nor need the peaks (frequencies and amplitudes) be as distributed for other species as they are in these three mosquito species, for example. Despite some common peaks, there is individuality among different species when it comes to detecting carbon dioxide.

Other species from different orders and different families have also been analyzed for their respective carbon dioxide detection abilities. Some are listed with their respective sum of intensities in Table 1. The species listed in Table 1 respond readily to carbon dioxide.

TABLE 1

Select insect species and the sum of the peak intensities as it relates to carbon dioxide detection (individual and composite graphs combined).

| Species | Order/Family (Type) | Sum of intensities |
|---|---|---|
| Aedes aegypti | Diptera/Culicidae (mosquito) | 389.7 |
| Anopheles gambiae | Diptera/Culicidae (mosquito) | 273.2 |
| Culex quinquefasciatus | Diptera/Culicidae (mosquito) | 289.0 |
| Diabrotica virgifera virgifera | Coleoptera/Chrysomelidae (beetle) | 300.3 |
| Rhodnius prolixus | Hemiptera/Reduviidae (bug) | 179.8 |
| Helicoverpa armigera | Lepidoptera/Noctuidae (moth) | 405.5 |

The scientific literature asserts that the moth, *Helicoverpa armigera*, has the most sensitive carbon dioxide reception among tested species (Stange, 1992; Rasch and Rembold, 1994). Our analysis supports this reported claim.

For comparative purposes, 25 other Gustatory Receptors from *Aedes aegypti* were analyzed to ascertain how many peaks coincided with the carbon dioxide peaks. Most of them showed weak similarity to the actual GRs that have been previously demonstrated to respond to carbon dioxide. The Sum of Intensities for the individual GR1, GR2, and GR3 receptors averaged 80.7. In contrast, all of the remaining GRs in *Aedes aegypti* achieved an average value of 21.2 (Sum of Intensities) thus revealing that not all Gustatory Receptors are universally responsive to carbon dioxide. Additionally, over 100 Pheromone Binding Proteins (PBPs) were individually analyzed and averaged a modest value of 23.4 (Sum of Intensities) relative to carbon dioxide detection while 415 Sensory Neuron Membrane Proteins (SNMPs) averaged 46.7 relative to carbon dioxide detection. It is apparent that some proteins are more specialized than others.

Water Detection in Arthropods

Much like carbon dioxide, water is another molecule having three atoms. Again, like carbon dioxide, water has absorption frequencies that are readily available. Utilizing these absorption frequencies, Sum of Intensities calculations may also be completed on any given protein receptor, in a similar way as calculated for carbon dioxide or water, for example. However, for this particular molecule, conducting differential analysis on separate states of matter (e.g., solid, liquid, gas), may further yield useful results.

The absorption frequencies for water may differ when it is in the liquid state versus when it is in the gas state (water vapor). One may use these differing peaks in order to calculate the different tendencies a given protein receptor has for the three states of water. Therefore, a comparative analysis may be calculated for liquid water vs. water vapor for any chosen protein receptor, for example. One may determine, for example, that the SNMP1 receptor proteins in Hymenoptera (e.g., wasps, bees, ants) may be weighted toward water vapor over liquid water (Sum of Intensities=85.7 for water vapor versus 25.9 for liquid water, where n=107). Similarly, the previously mentioned methods are able to distinguish that the SNMP2 receptor proteins in Hemiptera (true bugs) may be slightly more tuned to liquid water than they are to water vapor (Sum of Intensities=31.7 for liquid water versus 26.8 for water vapor, where n=18).

Odorant Receptors (ORs)

Arthropods generally can detect any odorant, which may be partly explained by an absorption spectrum of Odorant Receptors covering a large range of frequencies. There may be a small shift between absorption frequencies and emission frequencies, but given their close similarities, these terms will be used interchangeably for purposes of this disclosure.

The Indianmeal moth (*Plodia interpunctella*) genome was mapped in 2017, and an annotation of 42 of its Odorant Receptors was published in January 2018 (Jia et al., 2018). Forty-two Odorant Receptors are listed in the Supplementary Information for the online version of the January 2018 publication by Jia et al. (Supp. 4). Specifically, they are OR1, OR2, OR3 . . . . OR41, and OR43. (Id.) The Indianmeal moth ORCO is actually OR1 and so the Indianmeal moth ORCO was included in this OR analysis.

Each of the 42 Odorant Receptor spectra listed was quantified according to the amplitude of the respective peak(s) of each spectrum. There were 681 peaks obtained across the 42 spectra. If one considers each of these 681 peaks and their respective ranges, approximately 100% of the spectral range from 404 nm to 30 µm (micrometers or microns) is included under its "umbrella." This by itself would imply that the Indianmeal moth's odorant receptors may cover a full spectrum of possible odorants.

Upon closer inspection, more than half of the peak amplitudes are below five. If these relatively small peaks (59% of the 681 peaks) are excluded, 282 peaks remain. Even analyzing the remaining 282 peaks, it is still possible to calculate that 99.5% of the spectrum (from 404 nm to 30 µm) is covered by the Indianmeal moth's odorant receptors. Although this is less than 100% coverage, this difference of approximately 0.5% is relatively small, considering that 59% of the peaks were removed from consideration. This further implies that the smaller peaks may not affect olfaction significantly. An arthropod species may rely on the larger peaks when detecting odorants. Thus, while arthropods can detect virtually all frequencies emitted by odorants, certain frequencies may be detected more sensitively than other frequencies, depending on chemical compound and depending on arthropod species.

Another aspect of this analysis is that the extent of overlap from one Odorant Receptor (OR) spectrum to another is relatively small. Each of the 42 ORs in the Indianmeal moth had its own respective spectrum that was unique, with no substantial overlap over other ORs. This contrasted sharply with the carbon dioxide receptors analyzed above, as many of those peaks appeared repeatedly, no matter how unrelated some of the species actually may be from one another (beetles, moths, bugs, flies, etc.).

As noted above, a total of 681 peaks was obtained from the 42 ORs noted in the Indianmeal moth. The mean peak amplitude of these 681 peaks was 12.8. A cutoff point to determine a "major peak" may be determined based on the mean peak amplitude, in some embodiments. For example, a peak amplitude value of 20 and above may be considered a major peak, in the case of the Indianmeal moth for purposes of these experiments, but this may be varied depending on target number of peaks and level of coverage. Results of a stepwise analysis of all major peaks as defined above, referencing an electromagnetic range of wavelengths from 404 nm to 30 µm, are listed in Table 2.

TABLE 2

The percent coverage area between 404 nm and 30 µm for each of the peaks equal to or exceeding the specified value.

| Peaks used (minimum amplitude) | Coverage |
| --- | --- |
| 5↑ | 99.5% |
| 10↑ | 97.1% |
| 15↑ | 96.9% |
| 20↑ | 96.9% |
| 30↑ | 95.8% |
| 40↑ | 93.3% |
| 50↑ | 91.9% |
| 60↑ | 91.7% |
| 70↑ | 91.3% |
| 80↑ | 86.4% |
| 90↑ | 86.3% |
| 100↑ | 85.8% |

What Table 2 is showing is large coverage (about 90%) within a given range (404 nm to 30 µm) by only 42 Odorant Receptors. In one example, analyzing peaks of amplitude 100 and up, 11 peaks remained. But even with just these 11 peaks, coverage is over 85% of the tested frequency spectrum. If including major peaks of 20 and above (an arbitrary cutoff for a major peak), the Indianmeal moth still has 96.9% coverage within this EMF range of the specified electromagnetic wavelengths. This particular analysis considers ORs only—other chemosensory membrane receptors (e.g., GRs, IRs, SNMPs,) are not included in this analysis.

Figure 6:
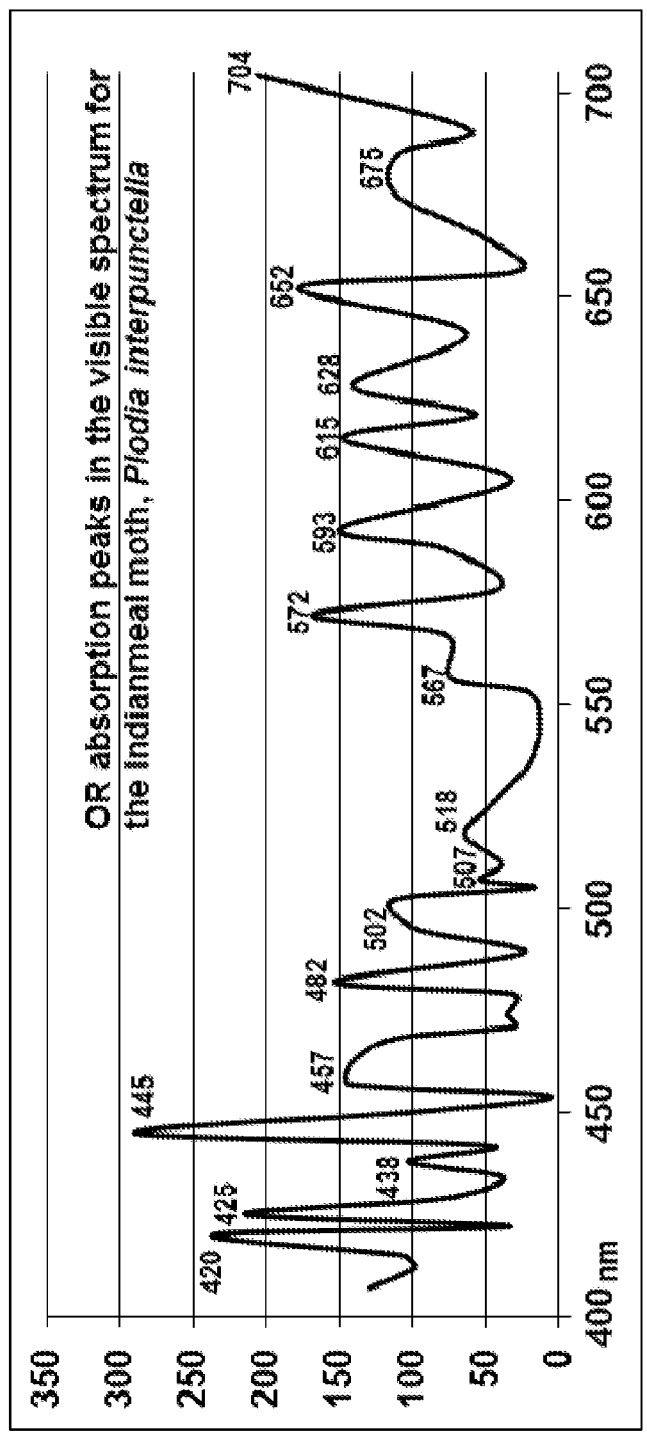
FIG. 6 is a composite, linear spectrum of all absorption frequencies for all of the Indianmeal moth Odorant Receptors in the visible range (400-700 nm) of the electromagnetic spectrum.
Figure 7:
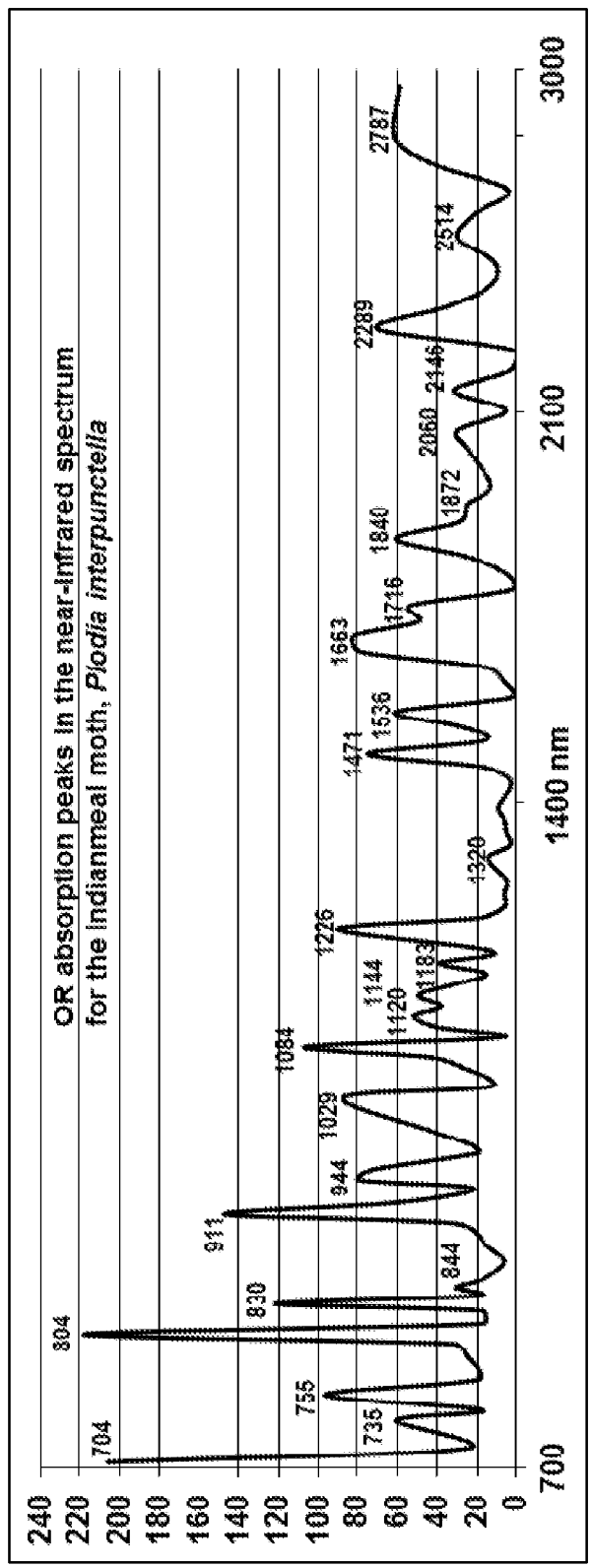
FIG. 7 is a composite, log-periodic spectrum of all absorption frequencies for all of the Indianmeal moth Odorant Receptors in the near-infrared range (700 nm-3000 nm) of the electromagnetic spectrum.
Figure 8:
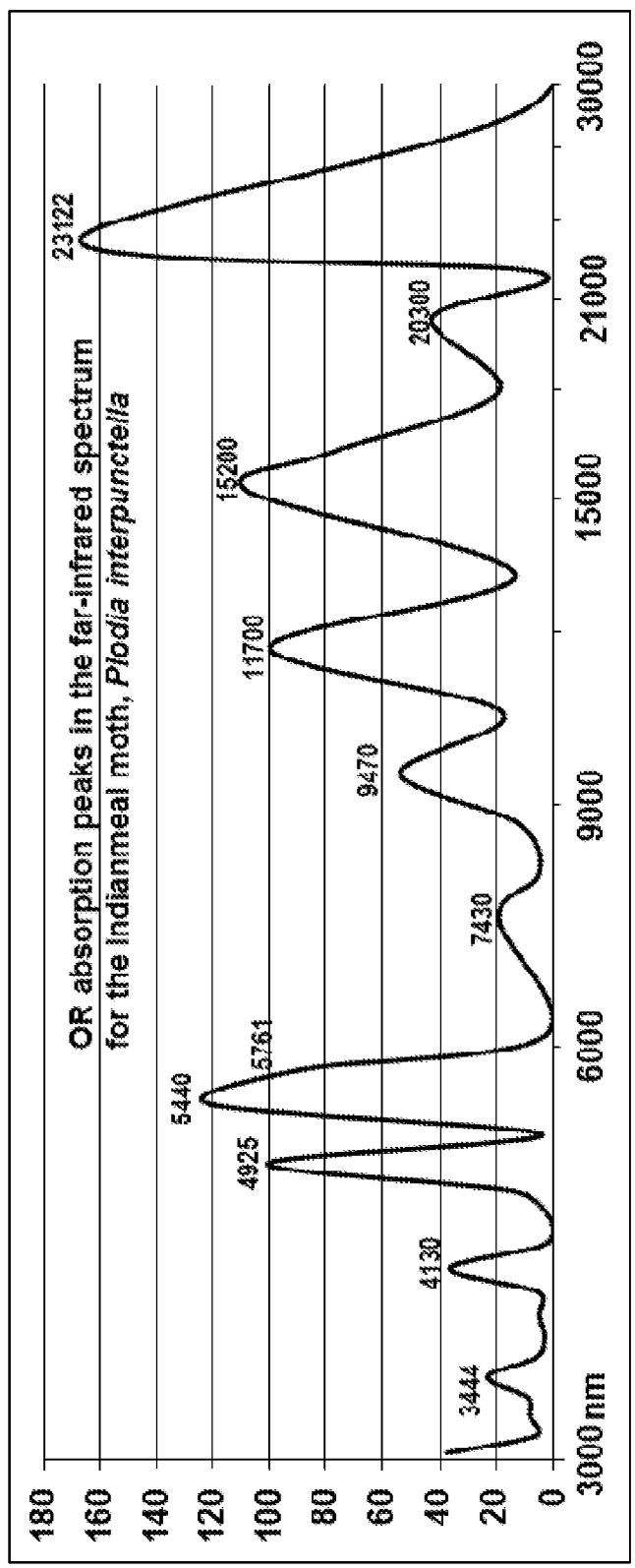
FIG. 8 is a composite, log-periodic spectrum of all absorption frequencies for all of the Indianmeal moth Odorant Receptors in the far-infrared range (3000 nm-30,000 nm) of the electromagnetic spectrum.

All 681 peaks are included in the following analysis and all peaks have an amplitude of at least 1, to ensure that the total spectrum for each of the 42 Odorant Receptors is included in this particular analysis. FIGS. 6-8 show spectral values for the Indianmeal moth's 42 Odorant Receptors within three different ranges: visible, near-infrared, and far-infrared, respectively.

FIG. 6 is a composite, linear spectrum of all absorption frequencies for all of the Indianmeal moth Odorant Receptors in the visible range (400-700 nm) of the electromagnetic spectrum.

FIG. 7 is a composite, log-periodic spectrum of all absorption frequencies for all of the Indianmeal moth Odorant Receptors in the near-infrared range (700 nm-3000 nm) of the electromagnetic spectrum.

FIG. 8 is a composite, log-periodic spectrum of all absorption frequencies for all of the Indianmeal moth Odorant Receptors in the far-infrared range (3000 nm-30,000 nm) of the electromagnetic spectrum.

These graphs have relative highs and lows (peaks and valleys). The valleys barely touch zero, indicating limited ability of the Indianmeal moth to detect frequencies emanating from molecules in this range, and peaks that rise well above average, indicating a collective high sensitivity to odorants possessing these concurrent peaks. As explained above in this disclosure, olfaction is a factor of detecting electromagnetic frequencies by dielectric resonance antennas (sensilla/antennae), which does not require physical presence of an actual chemical odorant. Thus, simulating these higher-amplitude peaks, in whole or in part, can therefore simulate olfaction, and can produce a directed behavioral effect. By decoding physical causes and behavioral effects of arthropods' (sensillar) olfaction, it is possible in turn to control arthropod behavior in a precisely targeted manner for particular species and behaviors, instead of indiscriminate, blanket deployment of chemical or electromagnetic attractants, anti-attractants, or repellants.

In the examples of FIGS. 6-8, the spectra shown are not simply spectra of select odorant receptors, such as OR7 or OR15. Instead, they are composite graphs of 42 known Odorant Receptors for the Indianmeal moth. This suggests that the particular peaks from FIGS. 6-8 may possess higher importance than peaks merely obtained from single spectra representing a single protein receptor.

Although it is not presently possible to know all odorants important to an Indianmeal moth, one in particular has a strong behavioral influence on the species: its pheromone. Listed in Table 3 are pertinent absorption peaks for the Indianmeal moth pheromone, a straight-chained 14-carbon acetate with two double bonds. For a general discussion of related concepts involving absorption peaks of pheromones and behavioral responses thereto, the description of U.S. patent application Ser. No. 14/014,065 (filed Aug. 29, 2013, entitled "Artificially Simulating Emissions of a Chemical Compound") is incorporated by reference.

TABLE 3

List of absorption peaks for the Indianmeal moth main pheromone component, (Z,E)-9,12-tetradecadienyl acetate as obtained by a Fourier Transform Infrared Spectrometer equipped with a spectral reflectance accessory. Original values were obtained in per-centimeter wavenumbers ($cm^{-1}$), but the wavenumbers have been translated to both microns ($\mu m$) and nanometers (nm) for convenience.

| wavenumbers ($cm^{-1}$) | microns ($\mu m$) | nanometers (nm) |
|---|---|---|
| 3008 | 3.3 | 3300 |
| 2925 | 3.4 | 3400 |
| 2854 | 3.5 | 3500 |
| 1740 | 5.7 | 5700 |
| 1452 | 6.9 | 6900 |
| 1386 | 7.2 | 7200 |
| 1365 | 7.3 | 7300 |
| 1223 | 8.1 | 8100 |
| 1037 | 9.6 | 9600 |
| 964 | 10.4 | 10400 |
| 723 | 13.8 | 13800 |
| 633 | 15.8 | 15800 |
| 605 | 16.5 | 16500 |
| 557 | 18.0 | 18000 |

Comparing absorption peaks for the pheromone against those of the Odorant Receptor Composite Peaks, one may observe that not all of the pheromone peaks are represented. A more thorough analysis of chemosensory receptors, including SNMPs, GRs, and IRs, may fill in any gaps in the electromagnetic spectrum. However, if only analyzing the ORs, one may observe that some of the pheromone's absorption peaks coincide closely with the peaks in the composite graphs. Specifically, they are 5700 nm, 7200 nm, 7300 nm, 9600 nm, 15,800 nm, and 16,500 nm. Each one of these six peaks also directly corresponds to those peaks representing the acetate component of the pheromone molecule. This strongly suggests that the acetate component of the pheromone is detected by the Odorant Receptors. Detection of the moth's pheromone may be a specific role of the ORs, at least as far as the Indianmeal moth is concerned.

The pheromones of lepidopterans (butterflies and moths) are virtually all straight-chained carbon backbones with either an alcohol side group, an aldehyde side group, or an acetate side group. Seeing how the Indianmeal moth Odorant Receptors code for an acetate molecule, thus corresponding to the structure of its own pheromone, one may extrapolate that the decoding of all other lepidopterans will similarly decode for other acetates, alcohols, or aldehydes with similar precision. In summary, in this manner, it may be possible to decode olfactory resonant frequencies for all of the pheromones of every arthropod species, or at least butterflies and moths. This aspect can be used to improve pest control, for example.

Figure 9:
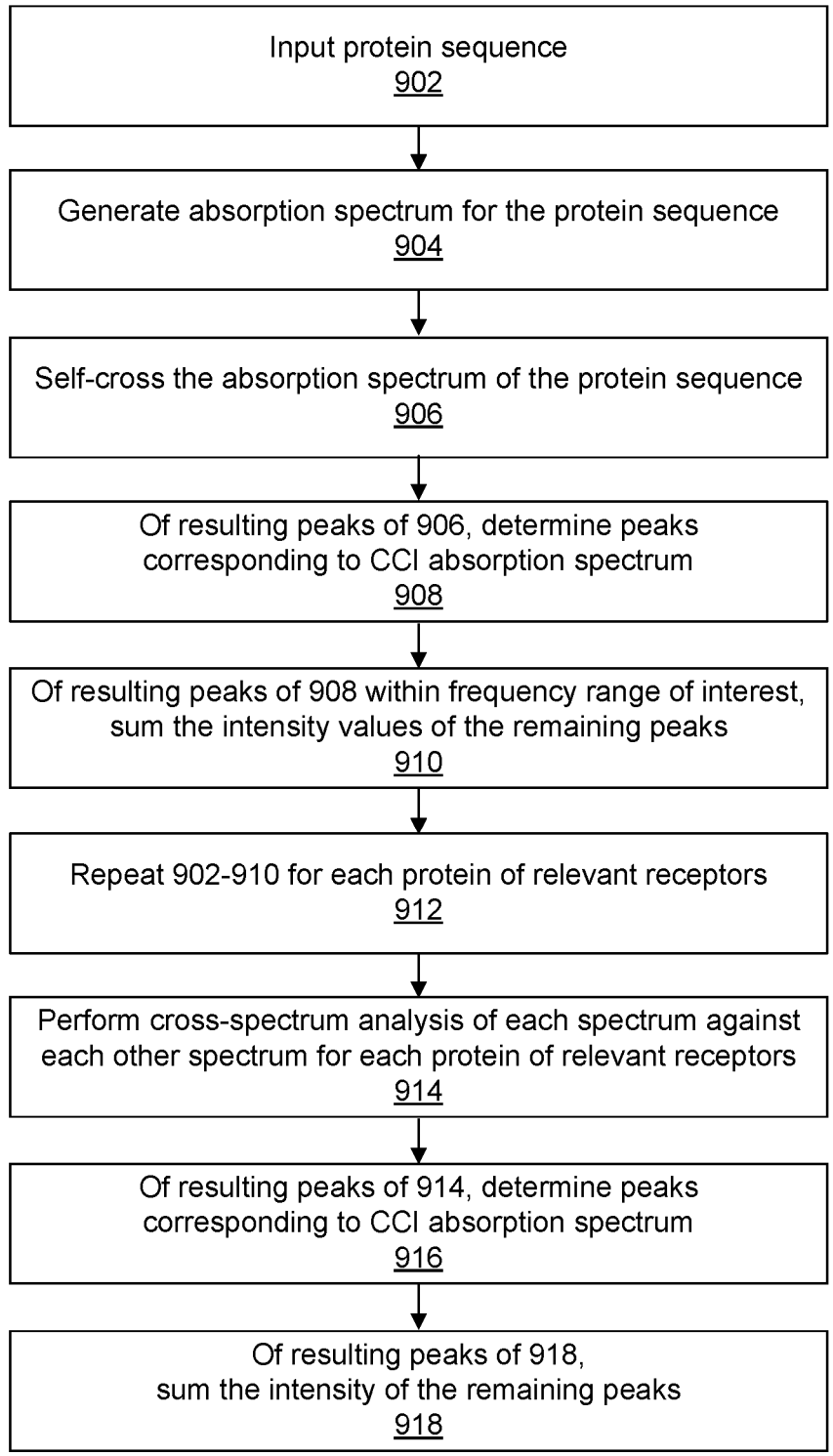
FIG. 9 is a flowchart illustrating a method for operation of the enhanced techniques of determining arthropod odorant olfaction as described herein, according to some embodiments.
Figure 10:
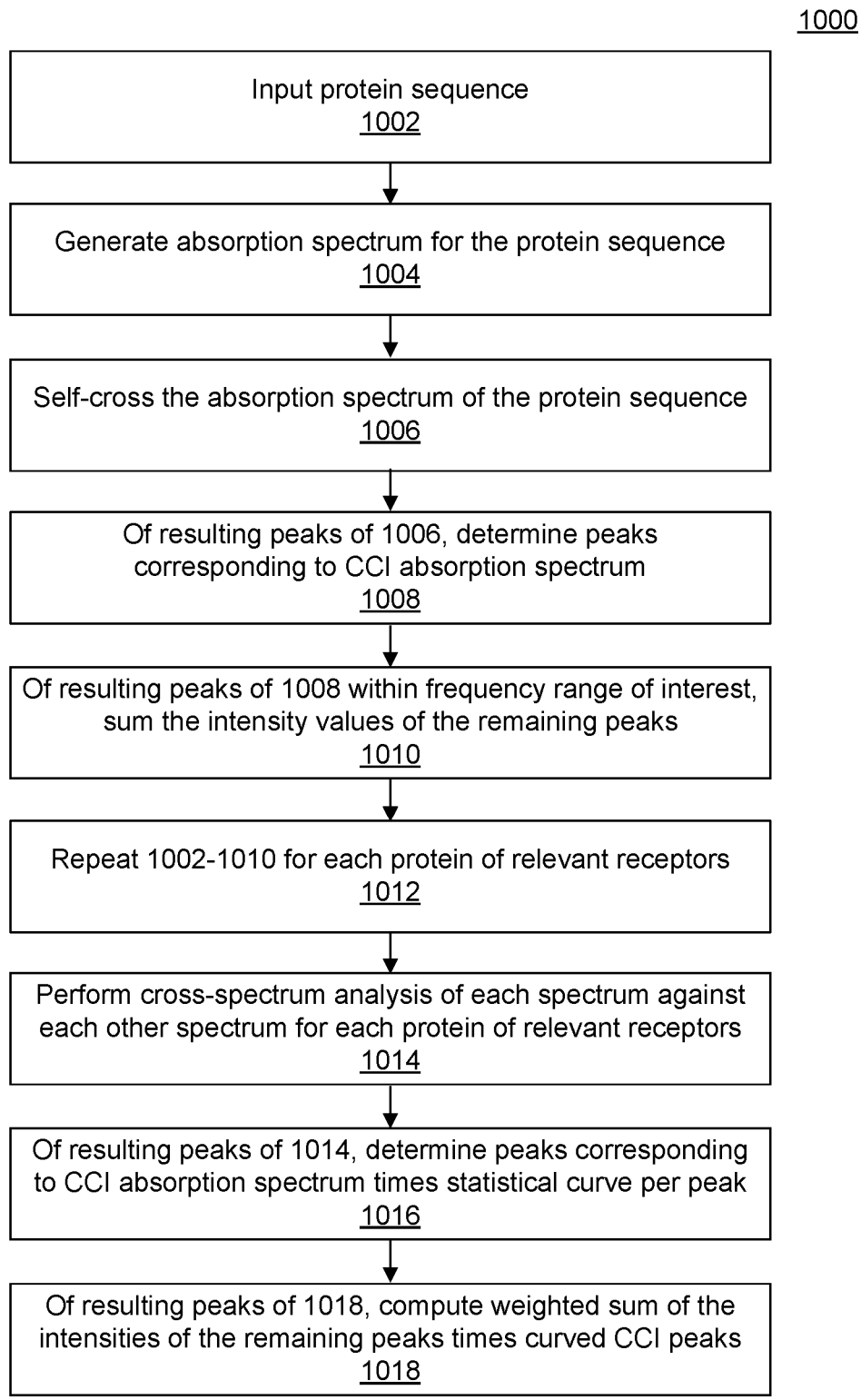
FIG. 10 is a flowchart illustrating a method for operation of the enhanced techniques of determining arthropod odorant olfaction described herein, according to some embodiments.

FIGS. 9 and 10 illustrate methods that may be used for determining olfactory chords and sensitivities, of a given arthropod species with respect to a given chemical compound of interest (CCI). The CCI may include, but is not limited to, an odorant or semiochemical, for example.

FIGS. 9 and 10 are flowcharts illustrating method 900 and method 1000, respectively, for operation of the enhanced techniques of determining arthropod odorant olfaction as described herein, according to some embodiments. Method 900 or method 1000 may be performed by processing logic that may comprise hardware (e.g., circuitry, dedicated logic, programmable logic, microcode, etc.), software (e.g., instructions executing on a processing device), or a combination thereof. Not all steps of method 900 or method 1000 may be needed in all cases to perform the enhanced techniques disclosed herein. Further, some steps of method 900 or method 1000 may be performed simultaneously, or in a different order from that shown in FIG. 9 or FIG. 10, as will be understood by a person of ordinary skill in the art.

At 902, a protein sequence may be used as input. The protein sequence may be digitally encoded in an electronic format, for example. In some embodiments, the format may be a standard or de facto common format, such as for compatibility with FASTA (Pearson), FASTX (FaBox), FASTQ (Wellcome), Solexa/Illumina, SSEARCH (Smith-Waterman), GGSEARCH (Global:Global), GL SEARCH (Global:Local), BLAST (Basic Local Alignment Search Tool), or any other sequence alignment tool or sequence format therefor.

The input may correspond to input of an algorithm, which may be automated in hardware, software, firmware, or any combination thereof, or may be performed or implemented in any other suitable manner. A protein sequence corresponding to an olfactory receptor may be used here as input, such as for determination of arthropod olfaction, although any protein sequence may be used generally for other purposes.

At 904, the input may be used to generate an absorption spectrum for the protein sequence, such as according to the algorithm described immediately above. The algorithm may include RRM, and may further be implemented in RRM software, for example. Additionally, or alternatively, the absorption spectrum may be generated at 904 by producing or retrieving it from other sources, such as libraries (public or private resources), other experimental data empirically determined and/or separately input, etc. In some embodiments, the absorption spectrum may focus on a range of frequencies, e.g., 404 nm to 30 $\mu m$, to provide one non-limiting example.

At 906, cross-spectrum analysis may be performed on the absorption spectrum generated at 904, with respect to the same absorption spectrum itself. This operation may also be referred to as self-crossing. To self-cross, a spectrum may be crossed against itself (may have cross-spectrum analysis run against a copy of itself) at least once. The self-cross operation may be iterated multiple times, e.g., 5×, in some embodiments. When operating with self-crossed spectra in relation to other self-crossed spectra, for example, such as when comparing or performing other mathematical operations, method 900 may be configured to self-cross each spectrum the same number of times at 906.

Figure 1:
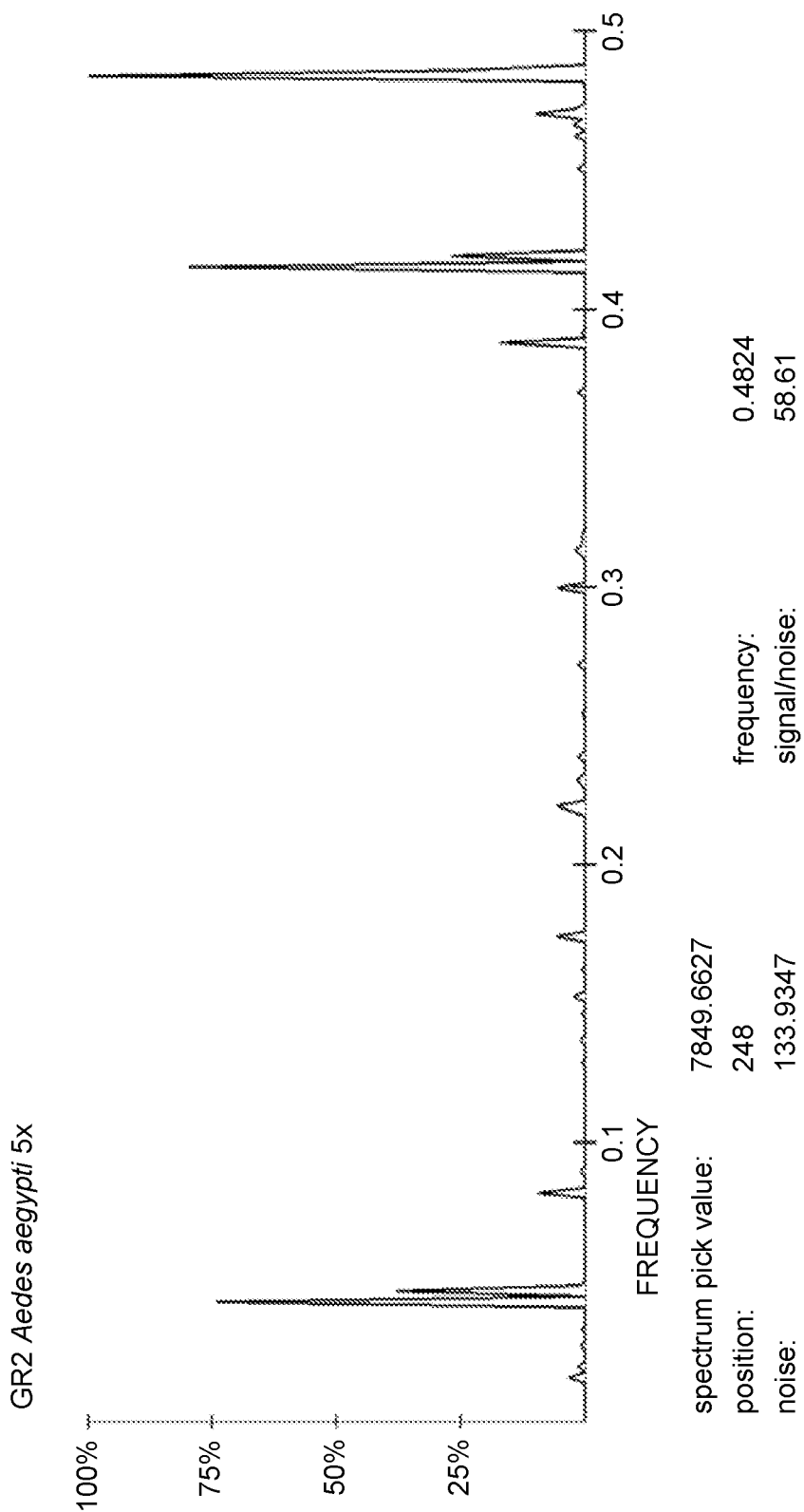
FIG. 1 represents one of these spectra.
Figure 2:
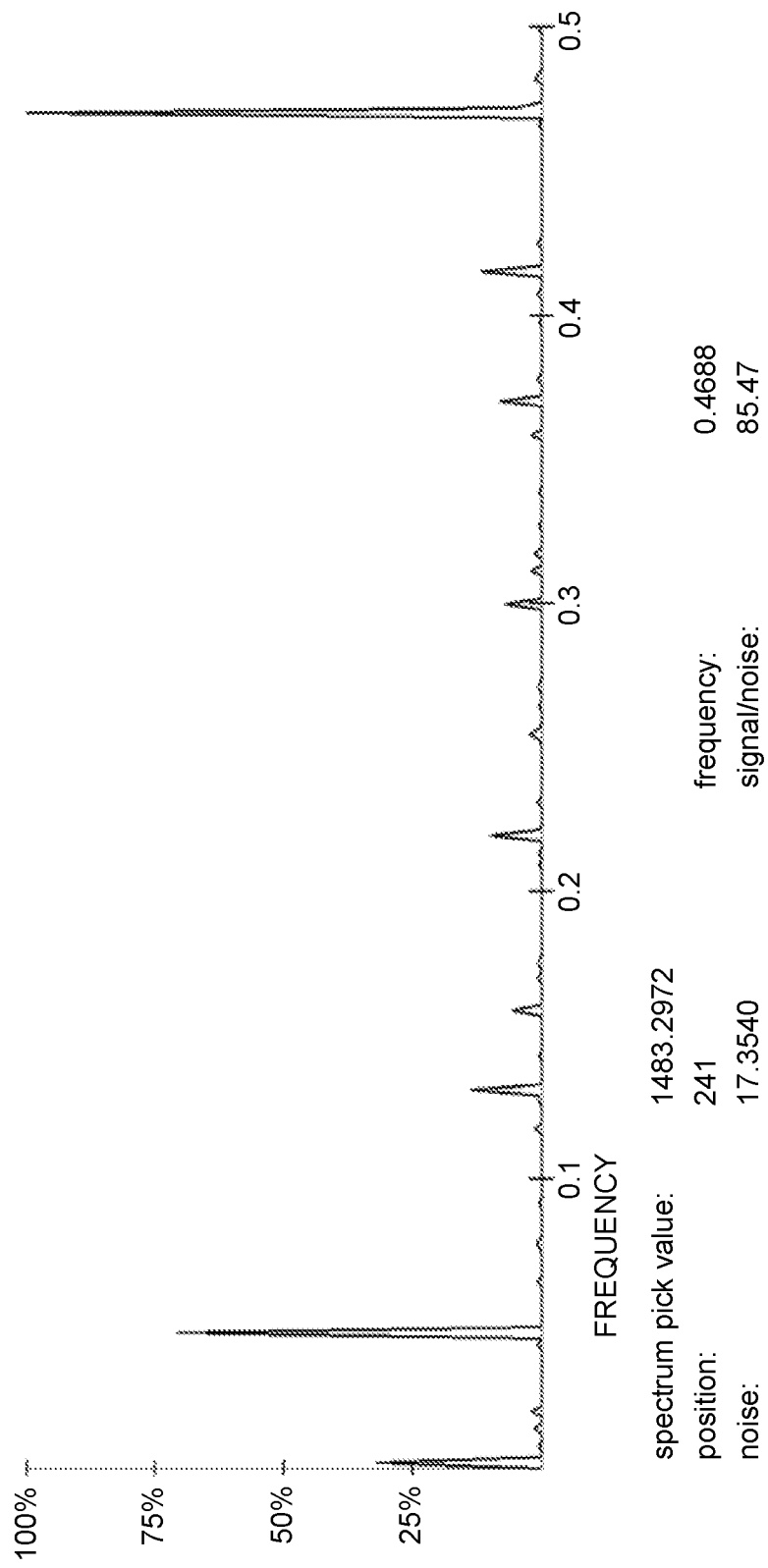
FIG. 2 is a composite spectrum featuring the crossing of three spectra representing GR1, GR2, and GR3 for the mosquito, *Aedes aegypti*. Two spectra from each of the GRs is crossed with one another resulting in a total of six crosses (6×).

At 908, of resulting peaks from the self-cross operation(s), peaks corresponding to a chemical compound of interest (CCI) may be determined. More specifically, the self-cross operations of 906 may result in a spectrum having multiple relative peaks (e.g., FIG. 1), while another chemical compound (e.g., $CO_2$, water, pheromone, etc.) has its own characteristic absorption spectrum. Relative peaks of the self-crossed protein spectrum may coincide with relative peaks of the CCI absorption spectrum, within specified tolerances for closeness of frequency and/or specific amplitude (or relative intensity). The frequencies of such coinciding peaks may be noted as frequencies to which the receptor corresponding to the analyzed protein is sensitive. Amplitude (intensity) of a given coinciding peak may correspond to a degree of sensitivity of the receptor to a frequency emitted in the emission spectrum CCI, for example.

At 910, an amplitude of each resulting peak of 908 may be summed. This sum of intensities for the coinciding peaks may be used as a proxy for overall sensitivity of the protein receptor to a given CCI, for example. At 910, there may be fewer peaks in the spectrum being analyzed, because the self-cross operation(s) and comparison to CCI absorption spectrum may eliminate or otherwise filter out many relative peaks in any of the spectra taken individually. Peaks at this stage may also be filtered by amplitude, in some embodiments. Thus, where fewer peaks remain, it may also be acceptable in some embodiments to use only the remaining peaks for calculating a sum of intensities, for example.

Figure 11:
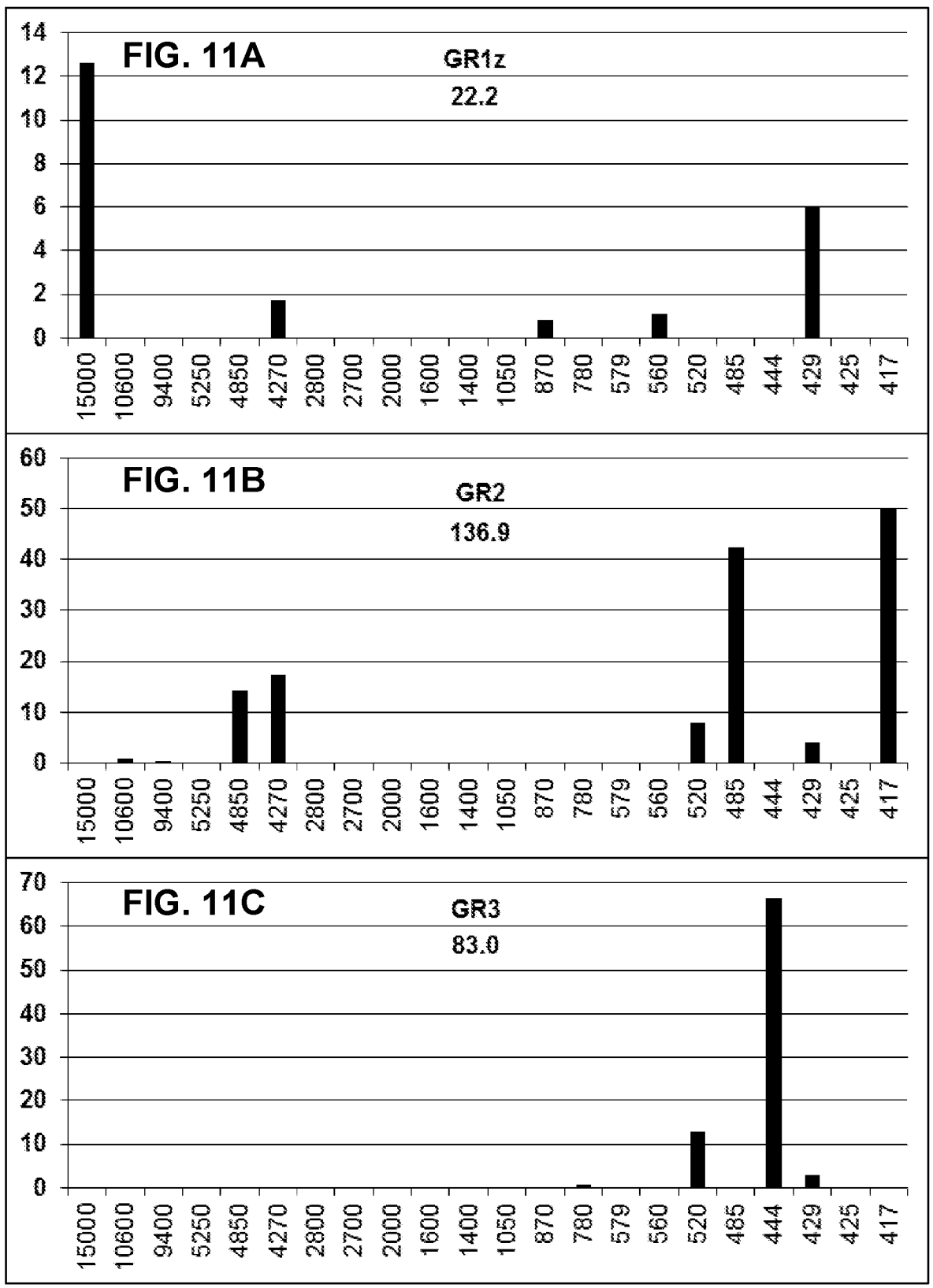
FIGS. 11A-11C show results of determining where absorption spectrum peaks of carbon dioxide correspond to peaks of absorption spectra for gustatory receptor proteins of GR1, GR2, and GR3, respectively, of *Aedes aegypti*.

At 912, 902-910 may be repeated for protein(s) of each relevant receptor. For example, if GR1, GR2, and GR3 are each relevant to detect a specific CCI in *Aedes aegypti*, and 902-910 were performed only for GR1. 902-910 may be repeated for GR2 and again for GR3. 912 may be continued until all proteins have been sufficiently analyzed to determine coinciding peaks (or lack thereof), in some embodiments. FIGS. 11A-11C show results of these operations for GR1, GR2, and GR3, respectively, of *Aedes aegypti* with respect to carbon dioxide.

Figure 12:
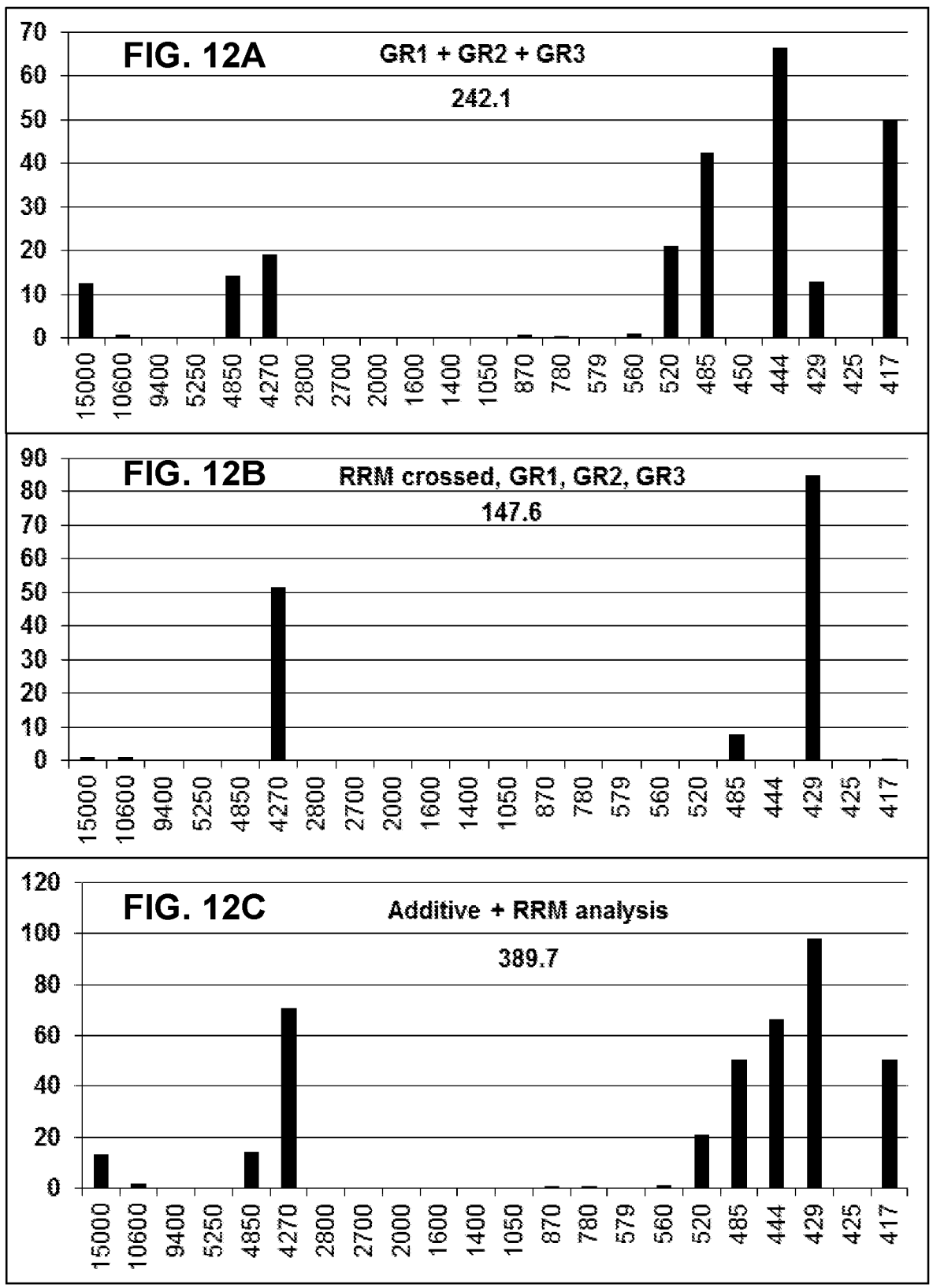
FIGS. 12A-12C show results of further processing for gustatory receptor proteins of GR1, GR2, and GR3, respectively, of *Aedes aegypti* with respect to carbon dioxide.

At 914, cross-spectrum analyses of each spectrum analyzed at 912 may be analyzed against each other spectrum analyzed at 912, for each protein of relevant receptors. In the $CO_2$-*Aedes aegypti* example of immediately above, GR1, GR2, and GR3 are each analyzed at 912. At 914, in this example, the absorption spectrum of GR1 may be crossed against the absorption spectrum of GR2, and the absorption spectrum of GR1 may also be crossed against the absorption spectrum of GR3. Similarly, the absorption spectrum of GR2 may be crossed against the absorption spectrum of GR1, and the absorption spectrum of GR2 may also be crossed against the absorption spectrum of GR3, and so on, until each combination has had a cross-spectrum analysis performed. Additionally, each cross-spectrum analysis may be iterated for multiple times. As with the self-crossing of 904, repeated iterations of cross-spectrum analysis may be more reliable when held to the same number of iterations per crossed combination, e.g., 2× each, according to some embodiments. FIG. 12B shows examples of such cross-spectrum analysis, according to an embodiment.

At 916, resulting peaks of 914 may be compared with the absorption spectrum of the CCI, in a similar manner to 908, to determine relative peaks (by frequency and/or amplitude) of the cross-spectrum analysis that coincide with the absorption spectrum of the CCI. Thus, at 916, it may be possible to determine at least the frequencies of the olfactory chord for a given species with respect to a given CCI, for example. Per-peak intensities (specific amplitudes) may also be determined.

At 918, of the resulting peaks from 916, few may be remaining compared to the original absorption spectra. However, the intensity of each remaining peak may be added together to get a sum of intensities, which may also be useful for characterizing sensitivity of a given arthropod species to a given CCI.

Various embodiments may be implemented, for example, using one or more well-known computer systems. One or more computer systems, for example, to implement any of the embodiments discussed herein, as well as combinations and sub-combinations thereof. Additionally, such computer systems may be embedded in a radiation emitter device, such that the emitter is configured to emit radiation in accordance with the olfactory chord frequencies and/or amplitude(s) calculated at 916 and/or 918, in some embodiments.

An alternative embodiment is presented in method 1000 as shown in FIG. 10 and accompanying description below. In this alternative embodiment, weighted averages may be used to approximate olfactory sensitivity based on proximity (in the frequency domain) of peaks of the CCI absorption spectrum and surrounding frequencies to peaks of corresponding proteins being analyzed. This alternative embodiment is one of several variations possible for determining olfactory chords. While method 900 as shown in FIG. 9 may include an "all or none" numerical response similar to a digital code, method 1000 as shown in FIG. 10 provides a more nuanced way of calculating sums of intensities, accounting for when coinciding peaks do not all coincide exactly, but where they may be slightly offset.

Variations possible here are to approximate peak shapes (for relative peaks of the CCI absorption spectrum and/or the analyzed protein absorption spectrum) on a curve, such as a Gaussian curve or Gaussian distribution (normal distribution), Lorentzian distribution, or other comparable statistical curve or distribution. The farther away a CCI absorption spectrum peak is from its corresponding protein absorption spectrum peak, the less that peak is weighted in terms of its corresponding intensity value, and the less it factors into the sum of intensities. Thus, while total sums of intensities resulting from method 1000 may be less than those resulting from method 900, these values may, in some embodiments, more accurately reflect the relative contribution of a given CCI to olfaction in a given arthropod species, for example.

At 1002, a protein sequence may be used as input. The protein sequence may be digitally encoded in an electronic format, for example. In some embodiments, the format may be a standard or de facto common format, such as for compatibility with FASTA (Pearson), FASTX (FaBox), FASTQ (Wellcome), Solexa/Illumina, SSEARCH (Smith-Waterman), GGSEARCH (Global:Global), GLSEARCH (Global:Local), BLAST (Basic Local Alignment Search Tool), or any other sequence alignment tool or sequence format therefor.

The input may correspond to input of an algorithm, which may be automated in hardware, software, firmware, or any combination thereof, or may be performed or implemented in any other suitable manner. A protein sequence corresponding to an olfactory receptor may be used here as input, such as for determination of arthropod olfaction, although any protein sequence may be used generally for other purposes.

At 1004, the input may be used to generate an absorption spectrum for the protein sequence, such as according to the algorithm described immediately above. The algorithm may include RRM, and may further be implemented in RRM software, for example. Additionally, or alternatively, the absorption spectrum may be generated at 1004 by producing or retrieving it from other sources, such as libraries (public or private resources), other experimental data empirically determined and/or separately input, etc. In some embodiments, the absorption spectrum may focus on a range of frequencies, e.g., 404 nm to 30 µm, to provide one non-limiting example.

At 1006, cross-spectrum analysis may be performed on the absorption spectrum generated at 1004, with respect to the same absorption spectrum itself. This operation may also be referred to as self-crossing. To self-cross, a spectrum may be crossed against itself (may have cross-spectrum analysis run against a copy of itself) at least once. The self-cross operation may be iterated multiple times, e.g., 5×, in some embodiments. When operating with self-crossed spectra in relation to other self-crossed spectra, for example, such as when comparing or performing other mathematical operations, method 1000 may be configured to self-cross each spectrum the same number of times at 1006.

At 1008, of resulting peaks from the self-cross operation(s), peaks corresponding to a chemical compound of interest (CCI) may be determined. More specifically, the self-cross operations of 1006 may result in a spectrum having multiple relative peaks (e.g., FIG. 1), while another chemical compound (e.g., $CO_2$, water, pheromone, etc.) has its own characteristic absorption spectrum. Relative peaks of the self-crossed protein spectrum may coincide with relative peaks of the CCI absorption spectrum, within specified tolerances for closeness of frequency and/or specific amplitude (or relative intensity). The frequencies of such coinciding peaks may be noted as frequencies to which the receptor corresponding to the analyzed protein is sensitive. Amplitude (intensity) of a given coinciding peak may correspond to a degree of sensitivity of the receptor to a frequency emitted in the emission spectrum CCI, for example.

At 1010, amplitude of each resulting peak of 1008 may be summed. This sum of intensities for the coinciding peaks may be used as a proxy for overall sensitivity of the protein receptor to a given CCI, for example. At 1010, there may be fewer peaks in the spectrum being analyzed, because the self-cross operation(s) and comparison to CCI absorption spectrum may eliminate or otherwise filter out many relative peaks in any of the spectra taken individually. Peaks at this stage may also be filtered by amplitude, in some embodiments. Thus, where fewer peaks remain, it may also be acceptable in some embodiments to use only the remaining peaks for calculating a sum of intensities, for example.

At 1012, 1002-1010 may be repeated for protein(s) of each relevant receptor. For example, if GR1, GR2, and GR3 are each relevant to detect a specific CCI in *Aedes aegypti*, and 1002-1010 were performed only for GR1, may be repeated for GR2 and again for GR3. 1012 may be continued until all proteins have been sufficiently analyzed to determine coinciding peaks (or lack thereof), in some embodiments. FIGS. 11A-11C show results of these operations for GR1, GR2, and GR3, respectively, of *Aedes aegypti* with respect to carbon dioxide.

At 1014, cross-spectrum analysis of each spectrum analyzed at 1012 may be analyzed against each other spectrum analyzed at 1012, for each protein of relevant receptors. In the $CO_2$-*Aedes aegypti* example of immediately above, GR1, GR2, and GR3 are each analyzed at 1012. At 1014, in this example, the absorption spectrum of GR1 may be crossed against the absorption spectrum of GR2, and the absorption spectrum of GR1 may also be crossed against the absorption spectrum of GR3. Similarly, the absorption spectrum of GR2 may be crossed against the absorption spectrum of GR1, and the absorption spectrum of GR2 may also be crossed against the absorption spectrum of GR3, and so on, until each combination has had a cross-spectrum analysis performed. Additionally, each cross-spectrum analysis may be iterated for multiple times. As with the self-crossing of 1004, repeated iterations of cross-spectrum analysis may be more reliable when held to the same number of iterations per crossed combination, e.g., 2× each, according to some embodiments. FIG. 12B shows examples of such cross-spectrum analysis, according to an embodiment.

At 1016, resulting peaks of 1014 may be compared with the absorption spectrum of the CCI, in a similar manner to 1008, to determine relative peaks (by frequency and/or amplitude) of the cross-spectrum analysis that coincide with the absorption spectrum of the CCI, multiplied by at least one statistical curve (e.g., Gaussian, Lorentzian, etc.) depending on how closely the crossed spectra coincide. Thus, at 1016, it may be possible to determine a weighted average for the frequencies and amplitudes of the olfactory chord for a given species with respect to a given CCI, for example. Per-peak intensities (specific amplitudes) may also be determined per the statistical curves (distributions).

At 1018, of the resulting peaks from 1016, few may be remaining compared to the original absorption spectra. However, the weighted intensity of each remaining peak may be added together to get a weighted sum of intensities, which may also be useful for characterizing sensitivity of a given arthropod species to a given CCI, and which may in some embodiments more accurately reflect the contribution a given CCI to olfaction in a given arthropod species.

Various embodiments may be implemented, for example, using one or more well-known computer systems. One or more computer systems, for example, to implement any of the embodiments discussed herein, as well as combinations and sub-combinations thereof. Additionally, such computer systems may be embedded in a radiation emitter device, such that the emitter is configured to emit radiation in accordance with the olfactory chord frequencies and/or amplitude(s) calculated at 1016 and/or 1018, in some embodiments.

FIGS. 11A-11C show results of determining where absorption spectrum peaks of carbon dioxide correspond to peaks of absorption spectra for gustatory receptor proteins of GR1, GR2, and GR3, respectively, of *Aedes aegypti*. Thus, FIG. 11A shows an absorption spectrum (of relative peak frequencies and corresponding relative amplitudes) for GR1 of *Aedes aegypti*. FIG. 11B shows the absorption spectrum of GR2 for *Aedes aegypti*. FIG. 11C shows the absorption spectrum of GR3 for *Aedes aegypti*. These spectra reflect a singular spectrum for each GR protein, self-crossed 5×. The number below each GR indicator is the sum of intensities for each respective self-crossed spectrum.

FIGS. 12A-12C show results of further processing for gustatory receptor proteins of GR1, GR2, and GR3, respectively, of *Aedes aegypti* with respect to carbon dioxide. FIG. 12A is a bar graph depicting an additive analysis of GR1, GR2, and GR3 of *Aedes aegypti*. In FIG. 12A, the peaks of FIGS. 11A-11C are summed on the same graph axes. To the extent that GR1, GR2, and GR3 are used by *Aedes aegypti* to detect carbon dioxide, FIG. 12A shows a composite picture of frequencies that may play a part in this aspect of arthropod olfaction.

FIG. 12B shows a result of absorption spectra (per RRM analysis) of G1, G2, and G3 of *Aedes aegypti*, crossed against each other twice each. The result is a component of an olfactory chord, having relatively few peaks of large relative intensity compared to other frequencies in the each absorption spectrum of each protein that correspond to the CCI (carbon dioxide, in this example embodiment).

FIG. 12C shows a collective contribution of the additive analysis of FIG. 12A with the RRM analysis of FIG. 12B. In this example, the collective contribution may be determined also by additive analysis of FIG. 12A and FIG. 12B, adding each relative peak on the same axes. This spectrum as shown in FIG. 12C may depict arthropod odorant detection (olfactory detection of carbon dioxide by *Aedes aegypti* yellow fever mosquitoes) to a high degree of precision and accuracy. However, the spectra shown in FIGS. 12A and 12B, as determined by various methods, may also be useful for certain applications and may benefit from further ease of calculation, according to some embodiments. Questions of which spectra may be used for which purposes (e.g., in universal radiation emitters, etc.) may depend on specific factors of various use cases, for example.

A Universal Emitter for any Arthropod Species

To attract an arthropod effectively requires more than simply presenting it with a single, key frequency. On the flip side, presenting an intense full spectrum, or a wider spectrum than necessary, may also be insufficiently effective. In deciphering olfactory codes of certain arthropod species, it becomes clear that a given species can be more likely to respond to a particular suite of frequencies, or olfactory chord. This olfactory chord, if presented to an arthropod, should result in a behavioral response which might be attraction, repellency, or confusion (mating disruption).

In some embodiments, lasers, LEDs, or other electronic emitters of radiation may be used to artificially emit a programmed combination of frequencies resulting in a desired behavioral response from a particular species of arthropod. Individual frequencies can be reliably emitted by, for example, solid-state lasers. Additionally, or alternatively, LEDs may provide for individual frequencies. In some embodiments, emitters may be utilized together with optical filters, such as with a device and/or corresponding system constituting emitter 1300 as shown in FIG. 13. Revisiting the piano analogy from above, each one of these lasers or LEDs can be analogized to a single key on a piano. So long as a pianist has all 88 keys at their disposal, they will be able to play any piano piece ever written. Similarly, if an arthropod species has, e.g., 88 frequencies that it can detect, arthropods of that species will be able to smell any odorant to which they are exposed using this combinatorial code. Adding to this combinatorial code the ability to strike the piano keys with varying force, one may understand how this intensity relates to the peak amplitude of olfactory chords.

The control and expression of each of the 88 (or any number of) arbitrary frequencies, both digital and analog codes, can be done using a semiconductor-based microcontroller, in some embodiments. Furthermore, switching between one olfactory chord to another can be accomplished in less than a tenth of a second, for example. When this concept is implemented in a particular device, such as a trap-type device, one benefit may be for use at night where particular pest species may emerge at specific times of night.

The flight windows (mating flights) of many insects, for example, may be between 2 and 4 hours. If an emitter is programmed to emit a particular olfactory chord known to be attractive to a given arthropod species at a given time, then emit another olfactory chord known to be attractive to another arthropod species at another given time, it is possible to catch different insects selectively over the course of an entire night with the same device, in an embodiment. Arthropods captured may further include representatives of different Orders (i.e., beetles and flies), just as it could for insects from the same Order (i.e. only moths of various kinds).

Some criticisms of this analogy may be that there are an infinite number of electromagnetic frequencies, and that having a specific number (e.g., 88) of discrete frequencies may be inadequate, and that millions of frequencies of a continuous nature would be required instead. But the evidence presented above shows that arthropod olfaction can effectively be captured or simulated in discrete variables rather than as continuous variables. Because behavior-influencing olfaction can be simulated with just a few discrete frequency emissions as effectively as a broad, continuous spectrum, then it is more advantageous (efficient, cost-effective) to use the fewest number of frequencies needed to achieve a desired result of pest control, in some use cases.

Additionally, research in arthropod olfaction has already determined that individual units of olfactory detection can correspond to glomeruli in an arthropod's brain, for example. Such glomeruli can number between 35 and 160 in many insects, for example. Similarly, chemosensory receptors typically number fewer than 120 per species. These values do not match the millions of possibilities indicative when utilizing continuous variables, further evidencing that fewer discrete frequency emissions may be used, while still achieving a similar effect.

By way of further examples, there is a 15-μm peak associated with carbon dioxide, water, and the Indianmeal moth pheromone. So, considering that many of the olfactory chords have overlapping frequencies to greater or lesser degrees, a universal device may be constructed for all arthropods, even including ticks, mites, spiders, scorpions, centipedes, to name a few non-limiting examples, as all such arthropods have virtually identical sensilla. This broad range of pest control can be accomplished based on one design and a relatively small number of frequencies.

Also, per the examples of FIGS. 3-5, 10-13 frequencies may be utilized by certain mosquito species when detecting carbon dioxide, as mentioned earlier. Consider also that of these 10-13 frequencies, 4-6 peaks may be large enough to be considered "major" such that the subject mosquitoes may need at least these to detect carbon dioxide (see FIGS. 3-5 and accompanying description above). Production of an artificial carbon dioxide attractant (i.e., electromagnetic simulator of carbon dioxide emissions) may thus require just these few frequencies to be matched to any species with a known attraction to carbon dioxide.

The number of frequencies applicable to any arthropod-odorant relationship turn out similarly upon further experimentation, e.g., identifying a chord of 4-6 frequencies, in some embodiments. This estimate can also apply to a deterrent or repellant, such as DEET (N,N-Diethyl-meta-toluamide) in the same manner as with an attractant. Determining appropriate deterrent frequencies (Wright et al., 1971) for DEET, the most common insect deterrent in the world, may allow for repelling arthropod species with the same intensity as that with which they could be attracted.

The inherent nature of a laser beam may be understood to limit its usefulness as an omnidirectional emitter. But strategic placement of convex and/or concave mirrors easily overcomes any such limitations. Similarly, special lamps or light-emitting diodes (LEDs) may be able to serve a similar purpose. Any of this allows a universal emitter to attract or repel approaching arthropods from almost any angle.

A universal emitter for arthropods can be made in order to control the behavior of any arthropod species. In combination with microelectronics to control and vary the frequencies and chords, such a universal emitter can also generate uniquely programmed and/or predetermined responses to any arthropod species. Programming and control may be achieved through any interface, including an application programming interface (API), over local, wired, or wireless means. For example, an interface may be combined with the universal emitter such that the universal emitter may be remotely controlled from a mobile device (smartphone application) and changed from one species to another in a matter of seconds.

The universal emitter may operate unattended, e.g., in unattended mode. In some embodiments, the universal emitter may operate without any $CO_2$ tanks, water evaporators, compartments for pheromones, plant odorants, or insect deterrents, for example. If a different device needed such consumable parts, operation time would be limited, as these consumable parts may need to be refilled or replaced regularly, or at least when they naturally run out of consumable material. As a result of not depending on consumable materials, the universal emitter may prolong its service life while significantly reducing maintenance burden. Other benefits of the universal emitter may include reduced mass and volume overall, making it portable and accessible in various parts of the world, including remote agricultural fields in third-world countries. The power module may be run by from renewable energy sources, e.g., using photovoltaic cells to generate solar power, in some embodiments, which may reduce overall size and further improve portability by reducing dependence on heavy or unwieldy batteries, for example.

The universal emitter may represent a new generation of pest management devices, in some embodiments, and may exhibit considerable improvements over conventional traps that may rely upon escaping molecules, for example, because the universal emitter may be less affected by adverse weather conditions, in many cases. Rainstorms are practically a daily occurrence in the tropics, and such adverse weather may typically interfere with the spread of molecules or other particles (e.g., semiochemical substances) released from a trap, whereas emission of electromagnetic radiation may be generally more reliable even in a wide range of extreme weather conditions. This improved performance in virtually all weather conditions represents a dramatic improvement over previous technology.

Example Emitter

FIG. 13 is a schematic diagram of an example emitter 1300. The example depicted in FIG. 13 is tuned to four frequencies of carbon dioxide detection for the malaria mosquito, *Anopheles gambiae*, as a non-limiting example. Emitter 1300 may be configured for other numbers of frequencies and adjusted for different frequencies and/or amplitudes, for example. According to some embodiments, depending on configuration and/or capability of radiation source 1310 and tunable filter bank 1330, emitter 1300 may be a universal emitter, such as that described above.

Emitter 1300 may include at least one radiation source 1310. In some embodiments, radiation source 1310 may be a broadband radiation source, which may be implemented by at least one LED, laser, incandescent light source, fluorescent light source, or a combination thereof, for example. Radiation source 1310 may include, but is not limited to, sources capable of and configured to emit visible light. Additionally, or alternatively, infrared, ultraviolet, or other emission spectra of electromagnetic radiation are within the scope of this disclosure.

Radiation source 1310 may, in some embodiments, be coupled (or integrated) with a controller 1312. Depending on radiation source 1310, controller 1312 may be optionally omitted. If present and functionally (e.g., communicatively) coupled with the radiation source, controller 1312 may be configurable to adjust frequency, amplitude, on/off status, oscillation, signal period, and other properties of radiation emitted from radiation source. Further, in some embodiments, controller 1312 may be programmable, as described above with respect to the universal emitter, allowing change of configurations automatically and/or by remote input from a user.

Radiation emitted from radiation source 1310 may be transmitted to a radiation-transforming element such as splitter 1320. In some embodiments, in order to facilitate such transmission, splitter 1320 may be coupled to radiation source 1310 via a physical link or medium, such as fiber-optic cable 1314, which may further include at least one subminiature assembly (SMA) further facilitating transmission. However, for electromagnetic radiation, some embodiments may function sufficiently without any additional transmission medium or other link.

Splitter 1320 may be configured to split radiation emission spectra into multiple radiation signals at particular frequencies or wavelengths, and at particular relative intensities for each given frequency or wavelength that may be present in tunable filter bank 1330. Adjustment of amplitude may include applying a weighted average, as described elsewhere herein with respect to FIGS. 9 and 10, for example. In some embodiments, splitter 1320 may be configured to split input radiation into multiple outputs, each output having approximately equal amplitude. In such embodiments, amplitude (intensity) may be modulated according to a weighted average by at least one filter element of tunable filter bank 1330.

Tunable filter bank 1330 may include one or more filter elements, which may be tuned statically or dynamically for frequency and/or amplitude of radiation signals. The number of filter elements in tunable filter bank 1330 may be fixed or variable, in some embodiments. Output signals of tunable filter bank 1330 may be fed to concentrator 1340, which may re-combine filtered radiation from tunable filter bank 1340 into a single signal having modulated frequency and/or amplitude components, in some embodiments. Optionally, in further embodiments, output of concentrator 1340 may be processed through an optical element 150, such as a lens or gradient-index (GRIN) rod. In some embodiments, output may be a collimated beam of radiation. Non-collimated beams may also be suitable, at least in close proximity with target arthropods.

In some embodiments, carbon dioxide detection for the Yellow Fever Mosquito, *Aedes aegypti*, may be reduced to seven frequencies having wavelengths 417 nm, 429 nm, 444 nm, 485 nm, 520 nm, 4270 nm, and 4850 nm. Each of these frequencies may differ in intensity (amplitude). Therefore, each peak may be assigned a corresponding specific amplitude for simulation that may be generated by increasing or decreasing the power output for an individual frequency. For example, 417 nm may be assigned a peak amplitude of 50.5, as shown in FIG. 3. The remaining frequencies may be assigned accordingly with wavelengths and relative intensities as follows: 429 nm (98.0), 444 nm (66.4), 485 nm (50.4), 520 nm (21.0), 4270 nm (70.8), 4850 (14.2).

Using an embodiment of the method described above, additional frequencies may be added to this short list in order to improve carbon dioxide detection with greater accuracy. These additional frequencies may be added in whole or in part to the seven frequencies above so as to create a more refined carbon dioxide chord. The frequencies and their respective amplitudes may be assigned with wavelengths and relative intensities as follows: 15,000 nm (13.6), 10,600 nm (1.8), 9400 nm (0.2), 870 nm (0.8), 780 nm (0.6), and 560 nm (1.4).

According to another embodiment, such as with a device and/or corresponding system 1300 as shown in FIG. 13, carbon dioxide detection for the malaria mosquito, *Anopheles gambiae*, may be reduced to four frequencies with wavelengths and relative intensities as follows: 485 nm (69.0), 444 (88.8), 429 nm (43.8), and 417 nm (32.8).

In another embodiment, additional frequencies may be added to this short list of four *Anopheles gambiae* frequencies, in whole or in part, in order to improve carbon dioxide detection. These additional frequencies may include wavelengths and relative intensities as follows: 15,000 nm (10.4), 10,600 nm (12.8), 9400 nm (3.3), 4850 nm (2.8), 4270 nm (7.0), and 780 nm (2.5).

According to another embodiment, carbon dioxide detection in the mosquito *Culex quinquefasciatus*, may be reduced to seven frequencies having wavelengths and relative intensities as follows: 10,600 nm (33.4), 9400 nm (5.3), 4270 nm (130.6), 1400 nm (8.4), 520 nm (8.0), 485 nm (36.8), and 417 nm (53.0).

In another embodiment, additional frequencies may be added to the seven frequencies listed above in order to improve carbon dioxide detection in *Culex quinquefasciatus*. These additional frequencies may include wavelengths and relative intensities as follows: 15,000 nm (2.9), 4850 nm (4.1), 870 nm (2.2), 780 (2.5) 579 nm (1.4), and 444 nm (0.4).

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

References herein to "one embodiment," "an embodiment," "an example embodiment," "some embodiments," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

REFERENCES

Callahan, P. S. (1965a) Intermediate and far infrared sensing of nocturnal insects. Part I. Evidences for a far infrared (FIR) electromagnetic theory of communication and sensing in moths and its relationship to the limiting biosphere of the corn earworm, *Heliothis zea*. Ann. Entomol. Soc. Am. 58:727-745.

Callahan, P. S. (1965b) Intermediate and far infrared sensing of nocturnal insects. Part II. The compound eye of the corn earworm, *Heliothis zea*, and other moths as a mosaic optic-electromagnetic thermal radiometer. Ann. Entomol. Soc. Am. 58:746-756.

Callahan, P. S. (1965c) Far infrared emission and detection by night flying moths. Nature, 207:1172-1173.

Callahan, P. S. (1967) Insect molecular bioelectronics: a theoretical and experimental study of insect sensilla as tubular waveguides, with particular emphasis on their dielectric and thermoelectric properties. Misc. Public. Entomol. Soc. Amer. 5(7):315-347.

Callahan, P. S. (1968) A high frequency dielectric waveguide on the antennae of night-flying moths (Saturniidae). J. Appl. Optics 7:1425-1430.

Callahan, P. S., E. F. Taschenberg, and T. Carlysle (1968) The scape and pedicel dome sensors—a dielectric aerial waveguide on the antennae of the night-flying moths. Ann. Entomol. Soc. Am. 61:934-937.

Callahan, P. S. (1971) Far infrared stimulation of insects with the Glagolewa-Arkadiewa "mass radiator." Fla. Entomol. 54(2):201-204.

Callahan, P. S. (1975) Insect antennae with special reference to the mechanism of scent detection and the evolution of the sensilla. Int. J. Insect Physiol. & Embryol. 4(5):381-430.

Callahan, P. S. (1976) The antenna of insects as an electromagnetic sensory organ. Studies on the shoot borer *Hypsipyla grandella* (Zeller). Misc. Public. #101, Vol. II. J. L. Whitmore (ed.). pp. 31-41.

Callahan, P. S. (1985) Dielectric waveguide modeling at 3.0 cm of the antenna sensilla of the lovebug, *Plecia nearctica* Hardy. Appl. Optics, 24:1094-1097.

Callahan, P. S., T. C. Carlysle, and H. A. Denmark (1985) Mechanism of attraction of the lovebug, *Plecia nearctica*, to southern highways: further evidence for the IR-dielectric waveguide theory of insect olfaction. Appl. Optics, 24:1088-1093.

Callahan, P. S. (1991) Dielectric waveguide (open resonator) models of the corn earworm, sensilla: sensilla relationship to infrared coherent molecular scatter emissions from semiochemicals (Lepidoptera: Noctuidae). Ann. Entomol. Soc. Am. 84(4):361-368.

Erdelyan, C. N. G., T. H. Mahood, T. S. Y. Bader and S. Whyard (2012) Functional validation of the carbon dioxide receptor genes in *Aedes aegypti* mosquitoes using RNA interference. Insect Molec. Biol. 21(1):119-127.

Franco, M. I., L. Turin, A. Mershin, and E. M. C. Skoulakis (2011) Molecular vibration-sensing component in *Drosophila melanogaster* olfaction. PNAS 108(9):3797-3802.

Cosic I. Macromolecular Bioactivity: Is it Resonant Interaction between Macromolecules?—Theory and Applications, IEEE Trans. on Biomedical Engineering, 1994; 41, pp. 1101-1114.

Cosic I. The Resonant Recognition Model of Macromolecular Bioactivity: Theory and Applications, Basel, Birkhauser Verlag, 1997.

Cosic I. Virtual Spectroscopy for Fun and Profit, Biotechnology, 1995; 13, pp. 236-238.

Cosic I, Drummond A E, Underwood J R, Hearn M T W. A New Approach to Growth Factor Analogue Design: Modelling of FGF Analogues, Molecular and Cellular Biochemistry, 1994; 130, pp. 1-9.

Krsmanovic V, Biquard J M, Sikorska-Walker M, Cosic I, Desgranges C, Trabaud M A, Whitfield J F, Durkin J P, Achour A, Hearn M T. Investigation into the Cross-reactivity of Rabbit Antibodies Raised against Nonhomologous Pairs of Synthetic Peptides Derived from HIV-1 gp120 proteins, J. Peptide Res., 1998; 52(5), pp. 410-412.

Istivan T, Pirogova E, Gan E, Almansour N M, Coloe P J, Cosic I. Biological effects of a de novo designed myxoma virus peptide analogue: Evaluation of cytotoxicity on tumor cells, 2011; PLoS ONE 6 (9), art. no. e24809.

Cosic I, Pirogova E. Bioactive Peptide Design using the Resonant Recognition Model, Nonlinear Biomedical Physics, 2007; 1(7), doi: 10.1186/1753-4631-1-7.

Cosic I, Hearn M T W. "Hot Spot" Amino Acid Distribution in Ha-ras Oncogene Product p. 21. Relationship to Guanine Binding Site, J. Molecular Recognition, 1991; 4, pp. 57-62.

Cosic I, Pavlovic M, Vojisavljevic V. Prediction of "Hot Spots" in Interleukin-2, Based on Informational Spectrum, Characteristics of Growth Regulating Factors, Biochimie, 1989; 3, pp. 333-342.

Pirogova E, Vojisavljevic V, Caceres J, Cosic I. Ataxin active site determination using spectral distribution of electron ion interaction potentials of amino acids in Medical & Biological Engineering & Computing, Springer, Germany, 2010; 48(4), pp. 303-309 ISSN: 0140-0118.

Pirogova E, Istivan T, Gan E, Cosic I. Advances in methods for therapeutic peptide discovery, design and development, Current Pharmaceutical Biotechnology, Bentham Science Publishers Ltd., Netherlands, 2010; ISSN: 1389-2010, 12(8), pp. 1117-1127.

Cosic I. The Resonant Recognition Model of Bio-molecular Interactions: possibility of electromagnetic resonance, Polish Journal of Medical Physics and Engineering, 2001; 7(1), pp. 73-87.

Pirogova E, Vojisavljevic V, Istivan T, Coloe P, Cosic I. Review Study: Influence of electromagnetic radiation on enzyme activity and effects of synthetic peptides on cell transformation. MD-Medical data, 2010; 2(4), pp. 317-324.

Cosic I, Lazar K, Cosic D. Cellular Ageing—Telomere, Telomerase and Progerin analysed using Resonant Recognation Model, MD-Medical Data, 2014; 6(3), pp. 205-209.

Caceres J L H, Cosic I, Cosic D. Retroviral proteases viewed through the Resonant Recognition Model, MD-Medical Data, 2014; 6(2), pp. 117-123.

Cosic I, Cosic D. Balancing insulin stability and activity—rational approach, MD-Medical Data, 2014; 6(1), pp. 7-10.

Grant, G. R. M. (1948) The sensory pits of insects considered as dielectric wave guides and resonators to infra-red rays. Proc. Royal Soc. Queensland 60(8):89-98.

Guerenstein, P. G. and J. G. Hildebrand (2008) Roles and effects of environmental carbon dioxide in insect life. Annu. Rev. Entomol. 53:161-178.

Jia, X., X. Zhang, H. Liu, R. Wang, and T. Zhang (2018) Identification of chemosensory genes from the antennal transcriptome of Indian [sic] meal moth Plodia interpunctella. PLOS ONE 13(1):0189889.

Jones, W. D., P. Cayirlioglu, I. G. Kadow, and L. B. Vosshall (2007) Two chemosensory receptors together mediate carbon dioxide detection in Drosophila. Nature Letters 445:86-90.

Omondi, B. A., S. Majeed, and R. Ignell (2015) Functional development of carbon dioxide detection in the maxillary palp of Anopheles gambiae. J. Exp. Biol. 218:2482-2488.

Robertson, H. M. and L. B. Kent (2009) Evolution of the gene lineage encoding the carbon dioxide receptor in insects. J. Insect Sci. 9:1-14. Article 19

Stange, G. (1992) High-resolution measurement of atmospheric carbon dioxide concentration changes by the labial palp organ of the moth Heliothis armigera (Lepidoptera: Noctuidae). J. Comp. Physiol. A 171:317-324.

Rasch, Ch. and H. Rembold (1994) Carbon dioxide—highly attractive signal for larvae of Helicoverpa armigera. Naturwissenschaften 81(5):228-229.

Turin, Luca (1996) A spectroscopic mechanism for primary olfactory reception. Chemical Senses 21/6 (1996) p. 773-791.

Wright, R. H., D. L. Chambers, and I. Keiser (1971) Insect attractants, anti-attractants, and repellents. Can. Entomol. 103:627-630.

What is claimed is:

1. A computer-implemented method comprising:
    determining at least one resonant frequency of an arthropod sensory organ;
    determining an absorption spectrum of at least one odorant;
    applying to the absorption spectrum a frequency filter that eliminates frequencies below a given intensity value;
    of the frequencies remaining from the absorption spectrum, selecting frequencies corresponding to relative peaks in absorption intensity;
    recording an olfactory chord comprising a group of frequencies of the selected frequencies corresponding to the relative peaks in absorption intensity, wherein the group of frequencies in the olfactory chord comprises at least one specific frequency that matches the at least one resonant frequency of the arthropod sensory organ; and
    configuring at least one radiation source to emit electromagnetic radiation corresponding to the olfactory chord.

2. The method of claim 1, wherein frequencies of the electromagnetic radiation correspond to the group of frequencies in the olfactory chord.

3. The method of claim 2, wherein the electromagnetic radiation further corresponds to a relative intensity at each frequency in the group of frequencies of the olfactory chord, wherein the relative intensity of the radiation at each frequency in the group of frequencies corresponds to the absorption intensity of each relative peak of the absorption spectrum having a matching frequency in the group of frequencies.

4. The method of claim 1, wherein the filter eliminates any frequencies having absorption intensity below a threshold.

5. The method of claim 1, wherein the filter ensures a minimum range of frequencies remaining in the absorption spectrum.

6. The method of claim 1, wherein the at least one resonant frequency is determined based at least in part on a protein analysis of a species to which the arthropod belongs.

7. The method of claim 6, wherein the protein analysis comprises a transcriptome analysis corresponding to the arthropod sensory organ.

8. The method of claim 1, wherein the at least one radiation source comprises a laser emitter.

9. The method of claim 1, wherein the at least one radiation source comprises a light-emitting diode (LED).

10. The method of claim 1, wherein the at least one radiation source comprises an incandescent or fluorescent light source.

11. The method of claim 1, wherein the olfactory chord is selected to cause a first behavioral response in the species to which the arthropod belongs.

12. The method of claim 11, further comprising:
programmatically changing a configuration of the at least one radiation source to emit radiation corresponding to a different olfactory chord selected to cause a different second behavioral response in the arthropod or to cause the first behavioral response in a different arthropod species.

13. The method of claim 11, wherein the behavioral response comprises at least one of attraction, repulsion, confusion, or disruption of mating.

14. The method of claim 11, wherein to cause the behavioral response in the arthropod, the at least one radiation source emits electromagnetic radiation corresponding to the olfactory chord and does not rely on a physical presence of any chemical attractant, chemical repellant, or chemical odorant.

15. The method of claim 1, wherein the olfactory chord comprises the following:
a first frequency of wavelength 417 nm having a first relative intensity of 50.5;
a second frequency of wavelength 429 nm having a second relative intensity of 98.0;
a third frequency of wavelength 444 nm having a third relative intensity of 66.4;
a fourth frequency of wavelength 485 nm having a fourth relative intensity of 50.4;
a fifth frequency of wavelength 520 nm having a fifth relative intensity of 21;
a sixth frequency of wavelength 4270 nm having a sixth relative intensity of 70.8; and
a seventh frequency of wavelength 4850 nm having a seventh relative intensity of 14.2.

16. The method of claim 15, wherein the olfactory chord comprises the following:
an eighth frequency of wavelength 15,000 nm having an eighth relative intensity of 13.6;
a ninth frequency of wavelength 10,600 nm having a ninth relative intensity of 1.8;
a tenth frequency of wavelength 9400 nm having a tenth relative intensity of 0.2;
an eleventh frequency of wavelength 870 nm having a eleventh relative intensity of 0.8;
a twelfth frequency of wavelength 780 nm having a twelfth relative intensity of 0.6; and
a thirteenth frequency of wavelength 560 nm having a thirteenth relative intensity of 1.4.

* * * * *